(12) United States Patent
Solem

(10) Patent No.: US 10,888,423 B2
(45) Date of Patent: *Jan. 12, 2021

(54) LEFT HEART ASSIST DEVICE AND METHOD

(71) Applicant: Syntach AG, Schaffhausen (CH)

(72) Inventor: Jan Otto Solem, Bjärred (CH)

(73) Assignee: Syntach AG, Schaffausen (CH)

( * ) Notice: Subject to any disclaimer, the term of this patent is extended or adjusted under 35 U.S.C. 154(b) by 356 days.

This patent is subject to a terminal disclaimer.

(21) Appl. No.: 15/673,241

(22) Filed: Aug. 9, 2017

(65) Prior Publication Data
US 2018/0008408 A1    Jan. 11, 2018

Related U.S. Application Data

(63) Continuation of application No. 13/901,469, filed on May 23, 2013, now Pat. No. 9,757,233, which is a
(Continued)

(30) Foreign Application Priority Data

Mar. 25, 2010 (SE) .................................. 1050282

(51) Int. Cl.
*A61F 2/24* (2006.01)
*A61M 1/10* (2006.01)
(Continued)

(52) U.S. Cl.
CPC .............. *A61F 2/2451* (2013.01); *A61F 2/24* (2013.01); *A61F 2/2442* (2013.01);
(Continued)

(58) Field of Classification Search
CPC ... A61F 2/2451; A61F 2/2442; A61H 31/006; A61H 31/004; A61M 1/122; A61M 1/125
See application file for complete search history.

(56) References Cited

U.S. PATENT DOCUMENTS 6,322,553 B1    11/2001  Vito
7,144,363 B2    12/2006  Pai et al.
(Continued)

FOREIGN PATENT DOCUMENTS

EP    2060282 A1    5/2009
RU    2255767 C2    5/2000
(Continued)

OTHER PUBLICATIONS

United States Patent and Trademark Office, Notice of Allowance dated May 10, 2017 in U.S. Appl. No. 13/901,469, 11 pages.
(Continued)

*Primary Examiner* — William H Matthews
(74) *Attorney, Agent, or Firm* — Inskeep IP Group, Inc.

(57) ABSTRACT

A device, a kit and a method is presented for permanently augmenting the pump function of the left heart. The mitral valve plane is assisted in a movement along the left ventricular long axis during each heart cycle. The very close relationship between the coronary sinus and the mitral valve is used by various embodiments of a medical device providing this assisted movement. By means of catheter technique an implant is inserted into the coronary sinus, the device is augmenting the up and down movement of the mitral valve and thereby increasing the left ventricular diastolic filling when moving upwards and the piston effect of the closed mitral valve when moving downwards.

19 Claims, 21 Drawing Sheets

Related U.S. Application Data continuation of application No. 13/122,710, filed as application No. PCT/SE2011/050337 on Mar. 25, 2011, now abandoned.

(60) Provisional application No. 61/317,619, filed on Mar. 25, 2010.

(51) Int. Cl.
*A61M 1/12* (2006.01)
*A61H 31/00* (2006.01)

(52) U.S. Cl.
CPC ......... *A61H 31/004* (2013.01); *A61H 31/006* (2013.01); *A61M 1/10* (2013.01); *A61M 1/1068* (2013.01); *A61M 1/1008* (2014.02); *A61M 1/1049* (2014.02); *A61M 1/1055* (2014.02); *A61M 1/12* (2013.01); *A61M 1/122* (2014.02); *A61M 1/125* (2014.02)

(56) References Cited

U.S. PATENT DOCUMENTS

| | | | |
|---|---|---|---|
| 7,753,837 | B2 | 7/2010 | Melvin |
| 9,757,233 | B2 * | 9/2017 | Solem ................. A61M 1/10 |
| 2003/0205454 | A1 | 11/2003 | Hlavinka et al. |
| 2003/0225454 | A1 | 12/2003 | Mathis et al. |
| 2004/0024286 | A1 | 2/2004 | Melvin |
| 2004/0102840 | A1 | 5/2004 | Solem et al. |
| 2004/0254600 | A1 | 12/2004 | Zarbatany et al. |
| 2005/0010240 | A1 | 1/2005 | Mathis et al. |
| 2005/0060030 | A1 | 3/2005 | Lashinski et al. |
| 2005/0209690 | A1 | 9/2005 | Mathis et al. |
| 2006/0020336 | A1 | 1/2006 | Liddicoat |
| 2006/0041306 | A1 | 2/2006 | Vidlund et al. |
| 2006/0042406 | A1 | 2/2006 | Vidlund et al. |
| 2006/0129025 | A1 | 6/2006 | Levine et al. |
| 2006/0155159 | A1 | 7/2006 | Melvin |
| 2006/0271162 | A1 | 11/2006 | Vito et al. |
| 2007/0173930 | A1 | 7/2007 | Sogard et al. |
| 2008/0039904 | A1 | 2/2008 | Bulkes et al. |
| 2008/0081942 | A1 | 4/2008 | Pai et al. |
| 2011/0190879 | A1 | 8/2011 | Bobo et al. |

FOREIGN PATENT DOCUMENTS

| | | |
|---|---|---|
| WO | WO 00/66196 A1 | 11/2000 |
| WO | WO2000/066196 A1 | 11/2000 |
| WO | WO2006/133186 A2 | 12/2006 |
| WO | WO2007/016122 A2 | 2/2007 |
| WO | WO2008/091614 A1 | 7/2008 |
| WO | WO2009/120764 A2 | 10/2009 |

OTHER PUBLICATIONS

WIPO, International Preliminary Examining Authority (International Bureau), International Preliminary Report on Patentability dated Sep. 25, 2012 in International Patent Application No. PCT/SE2011/050337, 8 pages.

WIPO International Search Authority, International Search Report and Written Opinion dated Jun. 29, 2011 in International Patent Application No. PCT/SE2011/050337, 13 pages.

* cited by examiner

LEFT HEART ASSIST DEVICE AND METHOD

RELATED APPLICATIONS

This application is a continuation of U.S. patent application Ser. No. 13/901,469 filed May 23, 2013 entitled A Device, A Kit And A Method For Heart Support, which is a continuation of U.S. patent application Ser. No. 13/122,710 filed Oct. 18, 2011 entitled A Device, A Kit And A Method For Heart Support, which is the U.S. National Phase of and claims priority to International Patent Application No. PCT/SE2011/050337, International Filing Date Mar. 25, 2011, entitled A Device, A Kit And A Method For Heart Support, which claims priority to U.S. Provisional Application Ser. No. 61/317,619 filed Mar. 25, 2010, and Swedish application Ser. No. SE1050282-1 filed Mar. 25, 2010, both entitled Device, A Kit And A Method For Heart Support, all of which are hereby incorporated herein by reference.

FIELD OF THE INVENTION

The present invention relates to an intra-vascular blood circulation enhancing apparatus, a system for intra-vascular blood circulation enhancement and a method for enhancing left ventricular pump function of a patient. The present invention may specifically be used to enhance the pump function of the left ventricle as a permanent measure for treating a heart failure disease where the heart function is deficient.

BACKGROUND OF THE INVENTION

Where the heart function is chronically insufficient, there may be a need to permanently aid the heart function. Heart failure (HF), more often called Congestive Heart Failure (CHF), is in general a condition where the heart, is unable to support the body tissue with its metabolic demands and to sustain adequate blood pressure and cardiac output. The term Congestive relates to a congestion of blood and fluids in front of the pumping ventricles as a result of insufficient forward pumping, most often caused by disease of the left ventricle muscle. A peculiarity of heart cells is that they do not regenerate after damage or cell death, thus conditions have a tendency to worsen rather than heal after heart cell damage. There are many reasons for heart cell death, the most common cause is ischemic heart disease, a condition where the arteries feeding the heart muscle get clogged, causing myocardial infarctions (MI). Viruses may damage the muscle cells, and some diseases, for instance cardiomyopathy have unknown reasons. End stage of long standing high blood pressure may also cause end stage heart failure. Heart strengthening drugs like digoxin or treatment with diuretics help for a while, but are all only treating symptoms. CHF is a progressive untreatable, disabling and finally a deadly condition. According to the American Heart Association homepage, there are in the US at present more than 5 Million patients living with CHF and 550 000 are added every year. 40 000 in the US are in such a bad state that only a heart transplant will keep them alive. However, due to the limited number of suitable organs only 2500 transplants are done yearly in the US. One may extrapolate the numbers for the rest of the industrialized world.

Total artificial heart, where the whole native heart is excised and replaced with a mechanical device was introduced in the 1960's by DeBakey, in the 1980's by among others Jarvik and recently by Copeland (CardioWest, Total Artificial Heart). However, these devices are still based on complex designs and are very invasive to install in the patient. Failure in operation of the device is fatal.

There are other techniques supporting only the failing left ventricle, known as left ventricle assist devices (LVAD). The most popular LVADs are the Novacor and the HeartMate devices. Common for this devices is the demand for major open heart surgery utilizing extracorporeal circulation by means of a Heart- and Lung-machine while stopping (or excising) the heart. These are bulky devices, a Novacor weights 1.800 grams, a HeartMate 1.200 grams. There are smaller axial flow pumps available nowadays, the HeartMate II, the Jarvik 2000 and the MicroMed DeBakey VAD. In addition, major open heart surgery is still necessary to install and connect these devices to the left ventricle cavity and the aorta by means of large vascular grafts. The mentioned devices have almost exclusively been used as a bridge to a heart transplant due to high frequency of complications, high mortality and limited durability. Their use has also been limited because of high prices of up to 150 000 $ only for the device.

None of the devices for permanent implant described are feasible for minimal invasive catheter based insertion, on the contrary, they all involve major open heart surgery. There is obviously a demand for simpler devices, it is the scope of the here presented invention to omit major cardiac surgery and to allow implant with catheter technique.

Moreover, health care is permanently searching for improved devices and methods.

Hence, there is a need of an improved system and/or method for permanently enhancing or assisting left ventricular pump function of a heart of a patient. The system is advantageously not interfering with the cardiac cycle of the heart.

Hence, an improved system and/or method for permanently enhancing or assisting left ventricular pump function of a heart of a patient would be advantageous and in particular allowing for increased flexibility, cost-effectiveness, long-term function, and/or patient friendliness would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a medical device, a kit, a method, and a computer-readable medium, according to the appended patent claims.

Embodiments of the invention take advantage of an improved understanding of left ventricular pump action and the close relationship between the Coronary Sinus (CS), the Great Cardiac Vein (GCV) and the Mitral valve (MV). Embodiments of the invention are providing movement of the CS and the GCV and thereby the MV along the long axis of the left ventricle (LV) towards and/or away from the heart apex, in synchrony with the cardiac cycle. In some embodiments energy is provided for this assisting movement. The here described embodiments of permanent implants do not take over or replace the remaining left ventricular pump function, they rather augment, improve, enhance or support the remaining natural pump function by means of an at least partly increased up and/or down movement of the mitral valve that works as a blood displacement or propulsion piston, when it is closed during the systole.

The here presented innovation is based on recent understanding of how the left ventricle functions and also on utilizing an undiscovered favourable anatomy of the left heart. Modern catheter based technology is integrated in embodiments of the here described device, system and methods.

Modern imaging of the beating heart has contributed largely to the understanding of left ventricle pump action. The pumping force of the left ventricle has before been understood to be a result of the heart muscle contracting and squeezing (systole) around the amount of blood enclosed inside the left ventricle after closure of the mitral valve, increasing the pressure and thereby forcing the blood towards the aortic valve, forcing this to open and ejecting the blood into the ascending aorta. When the squeezing is completed, an intermission occurs (diastole), during which a new portion of blood enters the left ventricle cavity from the left atrium.

Ultrasound imaging and Magnetic Resonance Imaging (MRI) has revealed that this previously taught mode of function is not completely true. Instead, one may describe two types of pump action, a long axis and a short axis action. MRI can show that there is a movement of the atrioventricular mitral valve (MV) plane downwards along the left ventricle long axis that extends from the atrium towards the ventricle's lower end, the apex. The left ventricle muscle cells are pulling the whole mitral valve plane, including the mitral valve annulus and part of the left atrial wall (that is stretching) towards the heart apex. By pulling the closed mitral valve towards the heart apex, the mitral valve becomes a piston in a blood displacement pump.

The downwards movement of the mitral valve is in a healthy human up to approximately 2 centimetres. The downwards movement accelerates the blood column away from the left atrium and towards the aortic valve in a continuous movement. By means of MRI technology one is able to virtually mark separate pixels inside the blood column and follow their movement. It is possible to show that the blood column flows more or less continuously from the left atrium to the ascending aorta without ever stopping. The blood column is accelerated by the mitral valve piston moving up and down along the cardiac long axis, opening every time it takes a new scoop of blood in an upward movement to the atrium, and closing just before moving back toward the apex.

The inventor of the present application realized that the location of the Coronary Sinus (CS) and the Great Cardiac Vein (GCV), very close to the mitral valve, can be utilized for enhancement of the left ventricular pump function. For instance a downwards movement of the mitral valve substantially along the long axis of the left ventricle may be supported. By actively moving, or supporting a still existing natural cardiac movement of, the CS and the GCV downwards towards the apex one simultaneously can move the mitral valve in the same direction.

The Coronary Sinus and the Great Cardiac Vein represent the large veins of the heart. The arterial blood of the heart passes the capillaries (the smallest vessels of the heart) and then enters the venous plexus in the heart tissue wall. Then the venous blood flows together into veins located on the heart surface. Distally the cardiac veins are small but unite together into larger and larger veins before flowing into the GCV and the CS. All the venous blood from the heart pours into the CS and then flows through the coronary sinus ostium (orifice) into the Right Atrium (RA) on the right side of the heart.

The major part of the CS and part of the GCV is located on the left atrial side of the mitral valve annulus. This is the part of the LA wall that stretches in a healthy heart when the MV is moving down towards the apex. The GCV then crosses the MV plane and annulus towards the LV side and join the anterior inter-ventricular vein on the front side of the heart. Thus the CS and the GCV encircle at least $\frac{2}{3}$ of the MV circumference, substantially in the same plane as the mitral valve plane, and are attached or embedded in tissue adjacent to the mitral valve.

Since the ostium of the coronary sinus is on the right side of the heart in the RA, one has easy access to the CS, the GCV and their side branches of veins on the heart surface by puncturing a peripheral vein, e.g. in the groin on the neck or in an arm. By means of modern catheter based technique, embodiments of the here disclosed device may be placed in position adjacent the mitral valve without major cardiac surgery. As matter of fact it is possible to place the device while the patient is conscious using only local anaesthesia, a common practice for implanting pacemakers and Intra Cardiac Defibrillators (ICD).

According to one aspect of the invention, a medical device is provided for enhancing intra-cardiac blood circulation of a heart of a patient by permanently assisting left ventricular pump action. The device has at least one first anchor unit implanted in a cardiac vessel of said heart, e.g. a side branch of the coronary sinus (CS) or the great cardiac vein (GCV). The first anchor unit may be an expandable stent structure for anchoring the anchor unit in the cardiac vessel, and/or wherein the first anchor unit has at least one tissue anchoring element, such as a hook or barb.

In embodiments the device has at least one second anchor unit implanted in the cardiac vessel, wherein the second anchor unit is located in the CS or the GCV. The second anchor may serve in transferring force from a remote force generating unit.

Thus, the device has a force generating unit that is in communication with said first and second anchor units, wherein said force generating unit generates a force in dependence of a cardiac cycle of said heart. The anchor units receive said force in such a manner that an assisted movement of said cardiac vessel and thus said mitral valve in a mitral valve plane is provided in a direction to and from an apex of the heart. However, in a specific embodiment, the second anchor unit may also have an integrated electrical motor instead and the force generating unit is the motor, the device having a connecting unit between the motor and the first anchor for the communication, and wherein the force is provided by the motor. In turn, the integrated electrical motor is provided with electrical energy from a remote energy source by means of an electrical cable.

By means of the applied force, the mitral valve is during systole assisted to move the mitral valve plane along the long axis of the left ventricle (LV) towards an apex of the heart and/or during diastole assisted to move the mitral valve plane away from the apex by the force for assisting the pump action of the heart. The assisted movement is provided in a controlled manner to support a natural movement of the mitral valve. When the mitral valve movement towards the apex is at least partly assisted during systole, the (still existing) natural pumping force of the heart is augmented while ejecting blood into the aorta. When the mitral valve movement away from the apex is at least partly assisted during diastole, the natural filling of the left ventricle of the heart is supported. Thus the (still existing) natural pumping function of the heart is augmented by an improved filling degree. The force generating unit is operatively connected to a remote energy source to receive energy therefrom and to controllably provide the assisting movement in synchrony with the natural heart cycle.

In some embodiments the force generating unit is an actuating unit for providing the force as a mechanical force, and wherein the first anchor unit and the actuating unit are in communication via a connecting unit for transferring the force and providing the movement.

In some embodiments the force is a magnetic unit for providing the force as a magnetically induced force. In such embodiments, the two anchors are magnetic, and wherein the first magnetic anchor unit and the second magnetic unit in the CS or GCV are in magnetic communication for transferring the force and providing the movement. At least one magnetic anchor unit is an electromagnet. At least one of the electromagnets is arranged to change polarity in synchrony with the cardiac cycle. While the second electromagnet anchor always is located in the CS or GCV, the first magnet may be positioned in various locations. In some embodiments the first magnet is located inside a side branch of the vein system on the left ventricular wall, e.g. the IAV, it may also be located in the left ventricle attached to the LV wall, or in the right ventricle, the right atrium or the left atrium of the heart, or on the left ventricular outer wall of the heart. In other embodiments the first magnetic anchor may not be located in, but adjacent to the heart, such as on the pericardium, the diaphragm, the spine or thoracic cage, in the pleura or under the skin.

In some embodiments the device has a remote energy source, a control unit, and a sensor for measuring physiological parameters related to the cardiac cycle activity providing a sensor signal. The sensor signal is provided to the control unit which controls the force generating unit to provide the movement by energy from the remote energy source and based on the sensor signal. The remote energy source may have a mechanical section where rotational or linear motion is generated. The device further may have an extension unit extending from the mechanical section, wherein the mechanical section is the force generating unit and wherein the motion is transferred in operation of the mechanical section to the first and second anchor unit for the movement of the mitral valve plane via an extension unit. The remote energy source is controlled by the control unit to provide electrical energy a) to one or more electromagnetical anchor units affixed in relation to the mitral valve, or b) to at least one force generating unit arranged at or in the heart, to provide the movement of the mitral valve plane.

In another embodiment, the first anchor unit may be implanted in the GCV or its continuation, more specifically in the anterior interventricular vein (AIV), and the second anchor unit may be implanted in the CS. An elongate extension unit connects the first and second anchor units in a loop shape such that they are in mechanical communication. Thus, the part of the device that is located in the CS and the GCV geometrically forms a loop around ⅔ of the MV, and very close to it. The extension unit extends proximally beyond the second anchor unit to a mechanical actuator unit arranged to rotate the extension unit synchronized with the cardiac cycle, wherein the device has different operative positions upon rotation of the extension unit, including upon rotation of the extension unit in a first direction a diastole operative position where the loop shaped extension unit is flexed towards the left atrium and the CS, GCV and MV are moved towards the left atrium, and a second operative position where upon rotation of the extension unit in a second direction, opposite the first direction, where the loop shaped extension unit is flexed towards the LV apex and the CS, GCV and MV are moved towards the LV apex.

In some embodiments the device is a non-powered device. The force generating unit may be a resilient unit, and the first anchor unit may include a distal anchor unit. The distal anchor and a proximal anchor unit may be arranged in the AIV, CS and GCV. The resilient unit may be a loop connecting the distal and proximal anchor units, wherein the resilient unit has a relaxed position in an upper MV plane position spring loaded against a MV plane down position, such that the cardiac muscle force of the LV brings the loop to the down position, and the resilient unit assists during the diastole by assisting the LV diastolic filling by forcing the open MV up against the blood stream further in the direction of the LA. In other embodiments, the resilient unit may have a relaxed position in a lower MV plane position spring loaded against a MV plane up position, such that the cardiac relaxation force of the LV brings the loop to the up position, and the resilient unit assists during the systole by assisting the LV systolic contraction by forcing the closed MV down towards the LV apex.

The resilient unit may be initially locked by an integrated bioresorbable material, such as PLLA, Polyvinyl or Polylactid, in such a manner that the spring loaded action is first initiated when the resorbable material has at least partly been resorbed, such that the device has a delayed activation upon implantation.

According to another aspect of the invention, a kit is provided, for permanently enhancing or augmenting the left ventricular pump function of a heart. The kit includes an implantable heart assist device according to the first aspect of the invention, and a delivery system suitable for inserting the assist device into a patient including a guide wire, a guiding catheter, and an introducing catheter.

According to another aspect of the invention, there is provided a kit for permanently enhancing the left ventricular function of a heart. The kit comprises a left ventricular enhancement or augmentation system placed in the coronary sinus and in adjacent tissue able to move the mitral valve plane, its annulus and leaflets along the direction of the long axis of a left ventricle in synchrony with the electrocardiogram, an energy source and a delivery system for carrying the augmentation system to desired positions in the heart.

The kit may provide a package to a surgeon who is about to introduce an enhancement system into a patient. Thus the kit provides both implants that may be used for permanently treating the patient and a delivery system which may be used for inserting the implants. The enhancing unit may be mounted in the delivery system for storage, while the energy source may be packaged separately for connection during surgery. The kit may further comprise a guide wire for guiding insertion of the delivery system to the desired positions through the vascular system of a patient. The delivery system may also comprise a guiding catheter which is arranged to be pushed over the guide wire to the desired position. Also an introducing catheter for establishing access to the vascular system through energy source pocket is part of the kit. A valve that is prohibiting blood backflow but still allows a guide wire or a guiding catheter to pass through is included in the introducing catheter.

According to yet another aspect of the invention, a method is provided for permanently enhancing intra-cardiac blood circulation of a heart of a patient by assisting left ventricular pump action. The method includes generating a force in dependence of a cardiac cycle of the heart by means of a force generating unit, applying the force to an implant in a cardiac vessel proximity to and in tissue connection with a mitral valve of the heart for an assisted movement of the cardiac vessel and thus the mitral valve in a mitral valve plane in a direction to and/or from an apex of the heart.

The assisted movement may include a controlled movement of the mitral valve in a mitral valve plane substantially along a long axis of a left ventricle of the heart by the force.

The aforementioned controlled movement may in some embodiments include moving the mitral valve in the heart in a reciprocating movement during systole towards an apex of the heart and during diastole away from the apex for assisting the pump action of the heart.

The generating a force in dependence of a cardiac cycle of the heart may include detecting the natural action of the heart, such as by measuring an electrocardiogram, a blood pressure wave, a blood flow, or acoustic signals of the heart, and providing energy for displacement of the mitral valve in synchrony with the natural heart cycle. Thereby is the natural up and down movement of a mitral valve assisted during a heart cycle.

In another embodiment the assisted movement may include a controlled movement of the mitral valve in a mitral valve plane substantially along a long axis of a left ventricle of the heart by the force and in addition also in a short axis of a left ventricle.

This additional transversal controlled movement may in some embodiments include moving the lateral LV wall in the heart in a reciprocating movement during systole towards an inter-ventricular septum of the heart and during diastole away from an inter-ventricular septum for assisting the pump action of the heart along the short axis of a LV of a heart.

The generating of a force in dependence of a cardiac cycle of the heart may include detecting the natural action of the heart, such as by measuring an electrocardiogram, a blood pressure wave, a blood flow, or acoustic signals of the heart, and providing energy for displacement of the mitral valve in synchrony with the natural heart cycle. Thereby is the natural up and down movement of a mitral valve assisted during a heart cycle as well as the natural inwards and outwards movement of the lateral LV wall relative to an intra-ventricular septum, along the short axis of a LV.

According to a further aspect of the invention there is provided a method for permanently treating failure of a left ventricle in a patient. The method comprises inserting a left ventricular enhancement system into the coronary sinus and adjacent veins and tissue and arranging the enhancement unit in desired positions such that the enhancement unit may be connected to energy source means.

The method comprises transfer of external energy to the enhancement unit in the coronary sinus and the great cardiac vein in order to move the mitral valve up and down along an axis from the left atrium towards the left ventricular apex in synchrony with the natural heart cycle.

The method includes also insertion of an energy source under the skin. The method allows connection of electrical cables or device extensions for transferring power to the energy source in such a way that the energy source may be located under the skin but outside a vein.

Further the method involves transfer of electrical energy through the skin either by cable or electro-magnetic in order to store electrical energy in a battery under the skin.

In addition hereto the method comprises the use of computer chips and algorithms in order to detect the spontaneous cardiac cycle and guide the enhancing device in accordance to the heart cycle by means detecting an electrocardiogram.

A preferable method of placing an energy source would be to do this surgically through a small incision in the skin and make a small pocket in the subcutaneous tissue under the skin. Part of the method would be to use the same pocket to gain access to a vein by means of puncturing the introducer catheter into the vein through the pocket. Still another part of the method would be to get access to inside of the left heart by means of puncturing an artery in order to place anchors. Further it is part of the method to attach an anchor to the atrial septum in a natural persistent foramen ovale or to attach it to the atrial wall by means of hooks. Finally anchors may be attached to the inside of the ventricles or atria by means of hooks.

The method may comprise in some embodiments include inserting a first anchor unit of an implantable heart assist device according to the first aspect of the invention into the coronary sinus and/or adjacent veins and tissue, and arranging the force generating unit in a position remote of the anchor unit such that the reciprocal movement of the mitral valve is provided along an axis extending from the left atrium towards the left ventricular apex of the heart.

According to yet a further aspect of the invention a medical procedure is provided that includes delivering a medical device adapted to enhance intra-cardiac blood circulation of a heart of a patient by assisting left ventricular pump action. The procedure may comprise providing a medical system including the medical device of some embodiments of the first aspect of the invention that are supplied with external energy, and providing an energy source, as well as minimally invasively delivering the medical system in the patient.

The procedure may include providing a delivery system, such as the aforementioned kit for minimally invasively delivering the medical device in the patient, and minimally invasively delivering the force generating unit of the medical system in the patient by means of the delivery system, delivering the energy source, and connecting the energy source and the force generating unit.

The procedure may comprise using a delivery system that includes an introducer catheter with a valve, a guiding catheter and a guide wire, and introducing the introducer catheter at a puncture site into the vascular system of the patient, inserting the guide wire into the vascular system via the introducer catheter, navigating through the vasculature and the heart to a desired site, inserting the guiding catheter over the guide wire, withdrawing the guide wire, through the guide catheter delivering a first anchor unit at a distance from the mitral valve and delivering a second anchor unit at a mitral valve.

According to a further aspect of the invention, a computer-readable medium having embodied thereon a computer program for processing by a computer is provided. The computer program includes code segments for controlling a medical device for permanently enhancing intra-cardiac blood circulation of a heart of a patient by assisting left ventricular pump action. A code segment is provided for controlling a force generating unit to generate a force in dependence of a cardiac cycle of said heart for applying said force to an implant in a cardiac vessel proximity to and in tissue connection with a mitral valve of said heart for an assisted movement of said cardiac vessel and thus said mitral valve in a mitral valve plane in a direction to and/or from an apex of said heart.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the following accompanying drawings.

DESCRIPTION OF EMBODIMENTS

Figure 1A:
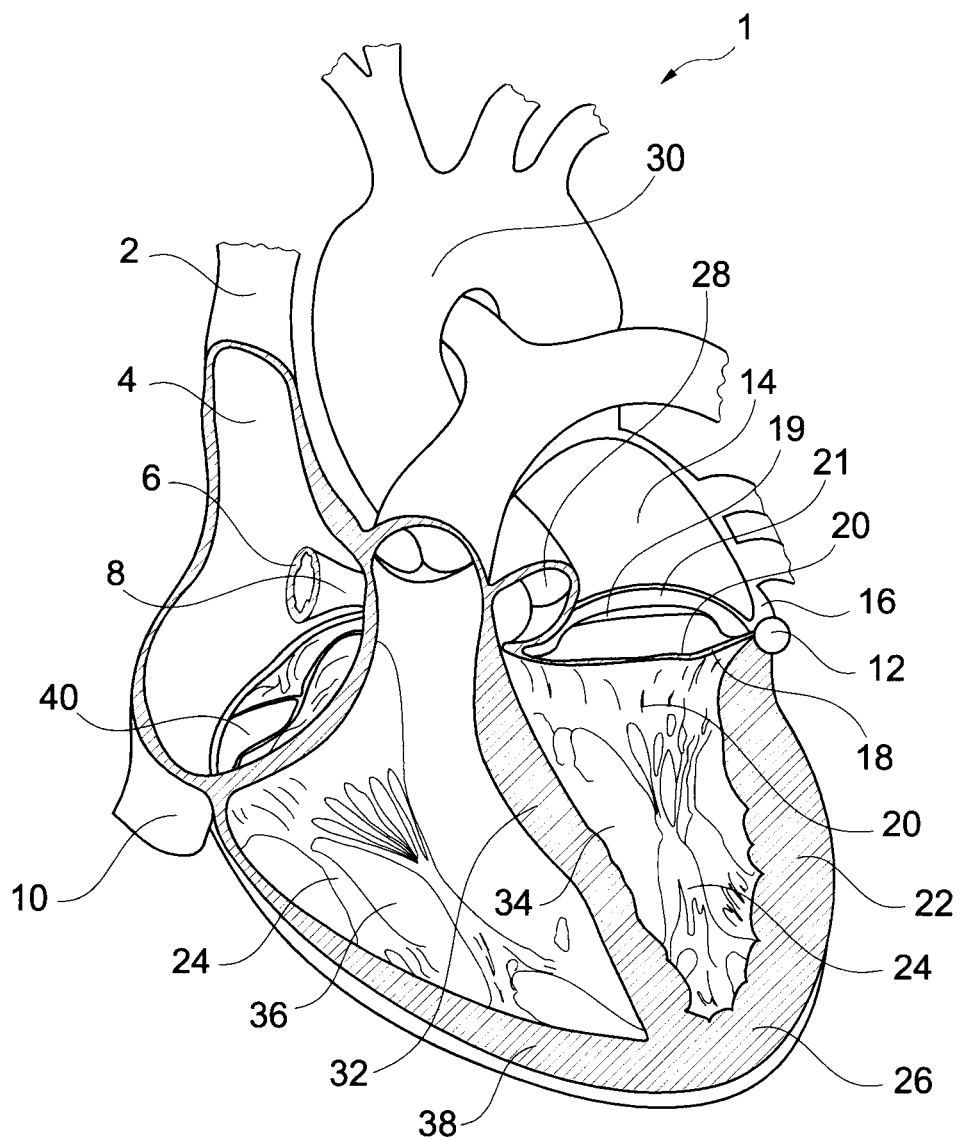
FIGS. 1a and 1b are schematic illustrations of the human heart depicting the cardiac anatomical structures that are involved.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Embodiments of the invention take advantage of new discoveries of left ventricular pump action and the close relationship between the Coronary Sinus (CS), the Great Cardiac Vein (GCV) and the Mitral valve (MV). Embodiments are by means of external power able to provide a movement of the CS and the GCV and thereby the MV along the long axis of the left ventricle (LV) towards the heart apex, in synchrony with the cardiac cycle. The here described permanent implant does not take over or replace the remaining left ventricular pump function, it will rather augment the pump function by means of an increased up and/or down movement of the mitral valve plane in relation to the long axis of the left ventricle.

Figure 1B:
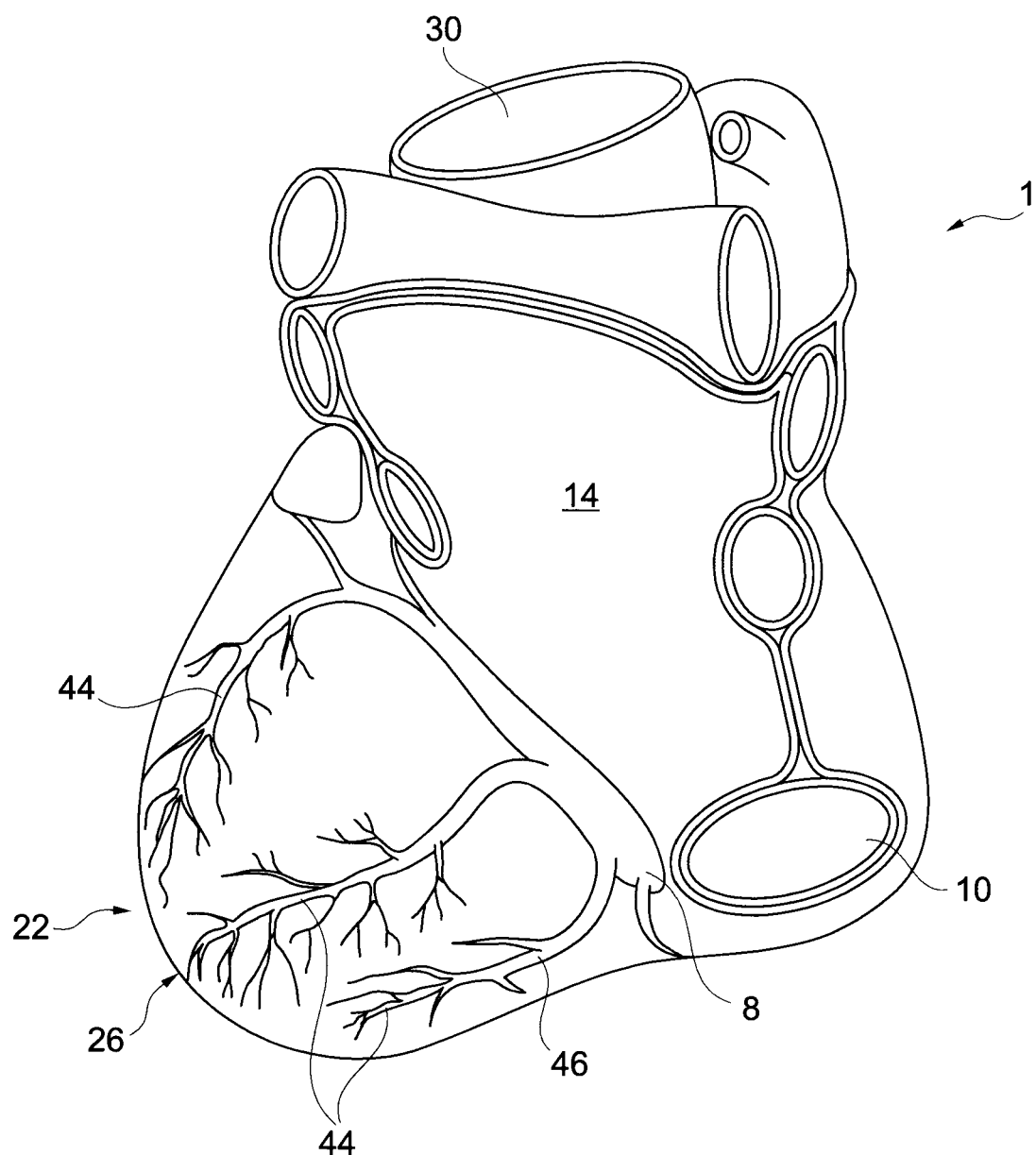

Now turning to the Figures, FIGS. 1a, 1b, 2a and 2b depict the structures of the heart 1 of which at least some are involved in embodiments of the invention. 2 is the Superior Vena Cava (SVC), 4 is the right atrium (RA), 6 is the CS ostium, 8 is the CS first part, the remaining part of the CS is behind the heart, e.g. depicted in FIG. 1b. 10 is the Inferior Vena Cava (IVC), 12 is the Great Cardiac Vein (GCV) at the level of the MV annulus 18. 14 is the Left Atrium cavity (LA), 16 is the LA wall, 18 is the mitral valve annulus, 19 the whole mitral valve, 20 is the anterior leaflet and 21 is the posterior leaflet of the mitral valve. 22 is the LV muscular wall, 24 are the papillary muscles, 26 is the apex of the left ventricle. 28 is the aortic valve, 30 the aorta ascendens, 32 the inter-ventricular muscular septum, 34 the left ventricular cavity and 36 the right ventricular cavity. 38 is the right ventricular muscular wall and 40 is the tricuspid valve.

Figure 2A:
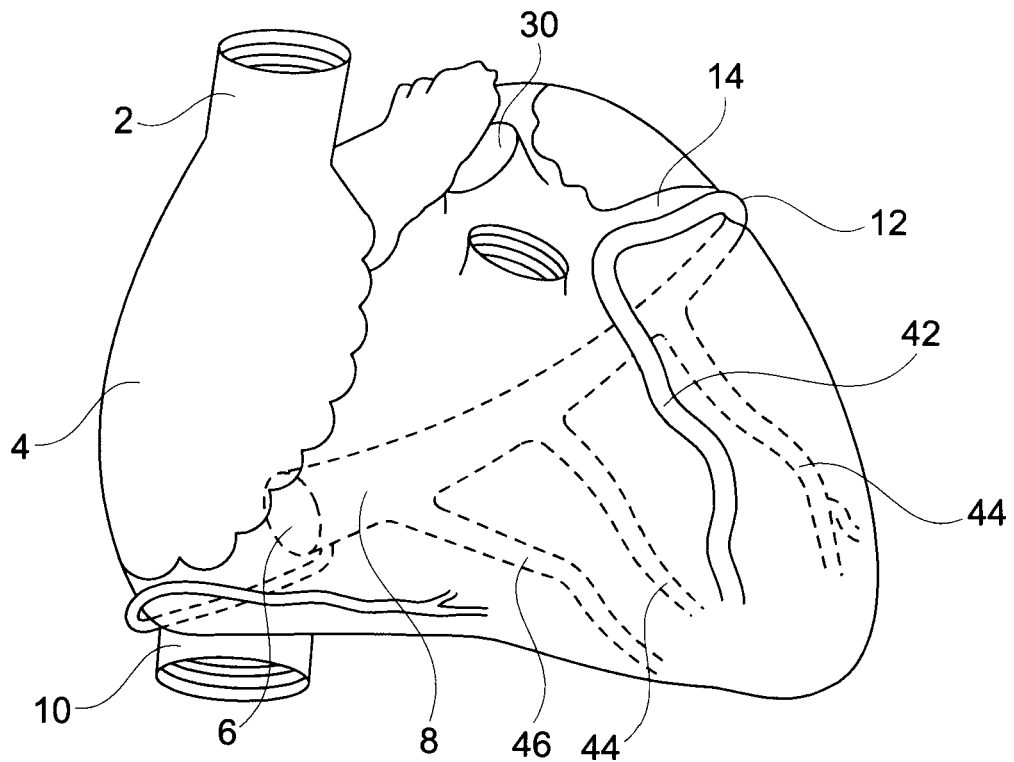
FIGS. 2a and 2b are schematic illustrations of the anatomy of the cardiac vein system including the coronary sinus, the great cardiac vein and the side branches as well as the level of the mitral valve plane in relation to the left ventricular axis.

FIGS. 1b and 2a show a schematic view of a heart, depicting the vein system, wherein reference numeral 42 is the anterior inter-ventricular vein, and 44 are lateral wall veins, side branches in the outside wall of the LV, 46 is the posterior descending vein. These side branch veins are also often referred to as the left marginal vein, the posterior veins of the left ventricle or the middle cardiac vein. However, they are all side branches of the CS or the GCV whatever they are called in the literature.

Figure 2B:
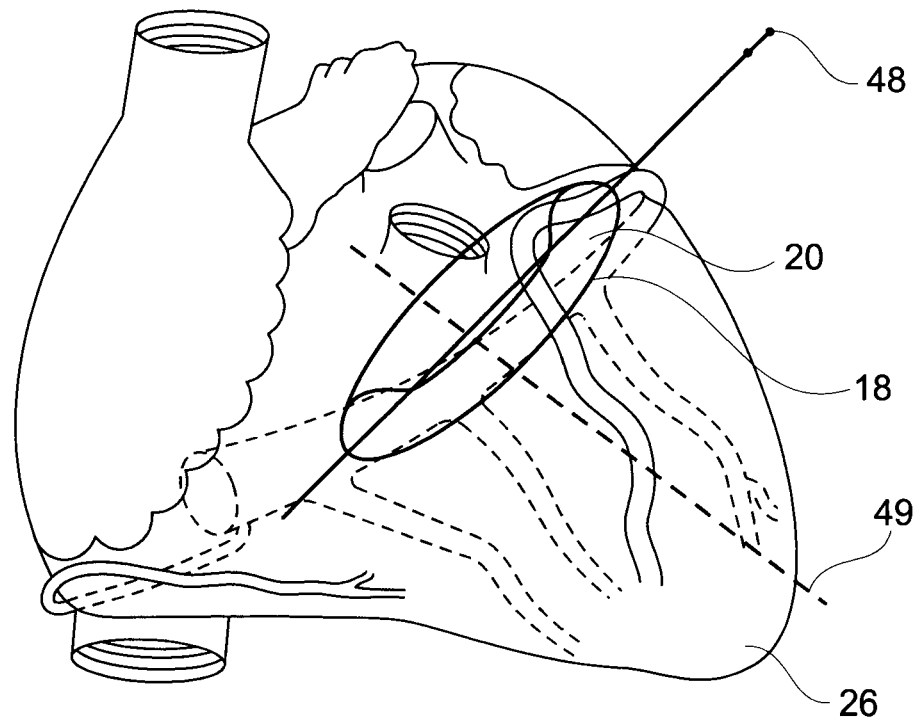

In FIG. 2b. the mitral valve plane 48 is shown in relation to the vein system and the LV long axis 49, which is close to perpendicular to the MV valve plane 48.

Figure 3A:
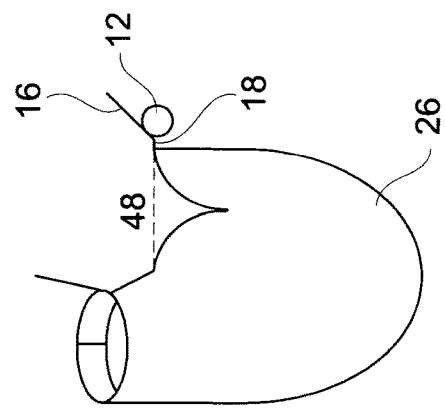
FIGS. 3a-c and 4a-c are schematic illustrations that explain the normal movement of the vein system of the heart and the mitral valve during a normal cardiac cycle.
Figure 3B:
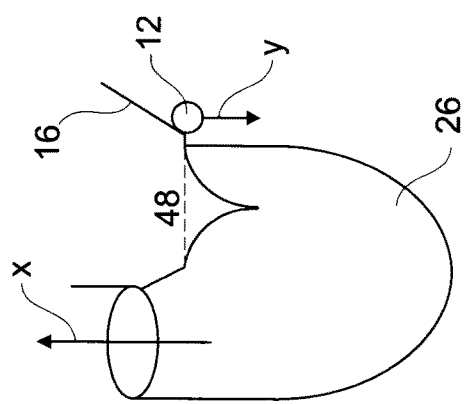
Figure 3C:
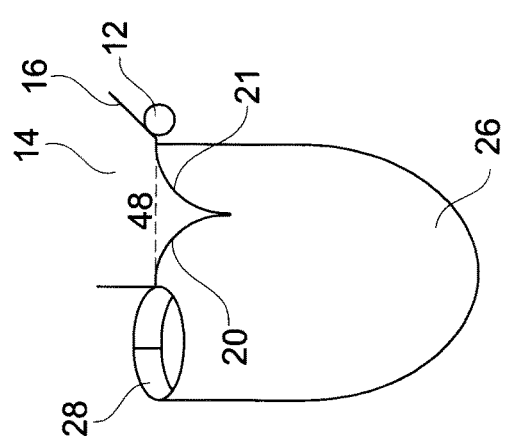

FIG. 3 is a schematic view of the movements in systole of the mitral valve plane 48 in relation to the LV apex 26, the GCV 12 (and CS) the MV anterior 20 and posterior 21 leaflets, the MV annulus 18, the aortic valve 28, the LA wall 16 and the LA cavity 14 during a normal heart beat. The large arrow x shows the direction of the blood flow and the small arrow y illustrates the direction of movement of the MV plane 48, the GCV and the CS until the end systole position is reached ("down" position). In the cardiac cycle, the following moments are shown in FIG. 3: a) is just before systole, b) during systole and c) end of systole.

Figure 4A:
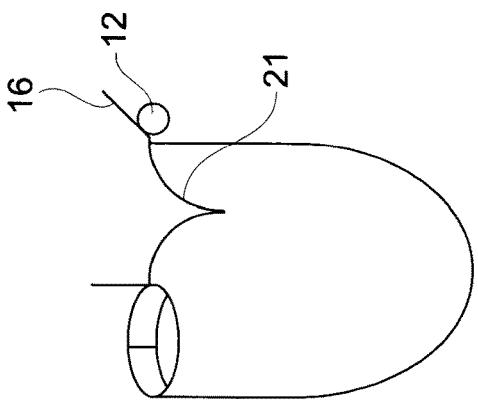
Figure 4B:
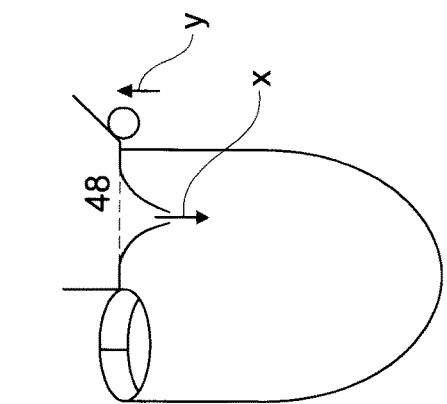
Figure 4C:
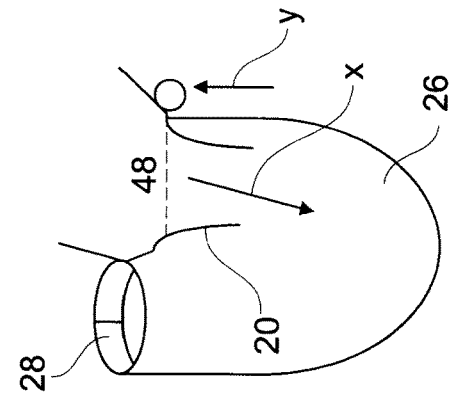

With reference to FIG. 4, a schematic view of the movements in diastole is shown of the mitral valve plane 48 in relation to the LV apex 26, the GCV 12 (and CS), the MV anterior 20, and posterior 21 leaflets, the MV annulus 18, the aortic valve 28, the LA wall 16 and the LA cavity 14 during a normal heart beat. The large arrow x shows the direction of the blood flow and the small arrow y the direction of movement of MV plane 48, the GCV and the CS, until the end diastole position is reached ("up" position). In the cardiac cycle, the following moments are shown in FIG. 4: a) early diastole, b) late diastole and c) end of diastole, at the end of diastole the mitral valve is now closed and ready for the next move downwards in the following systole.

Figures 5A, 5B, 5C:
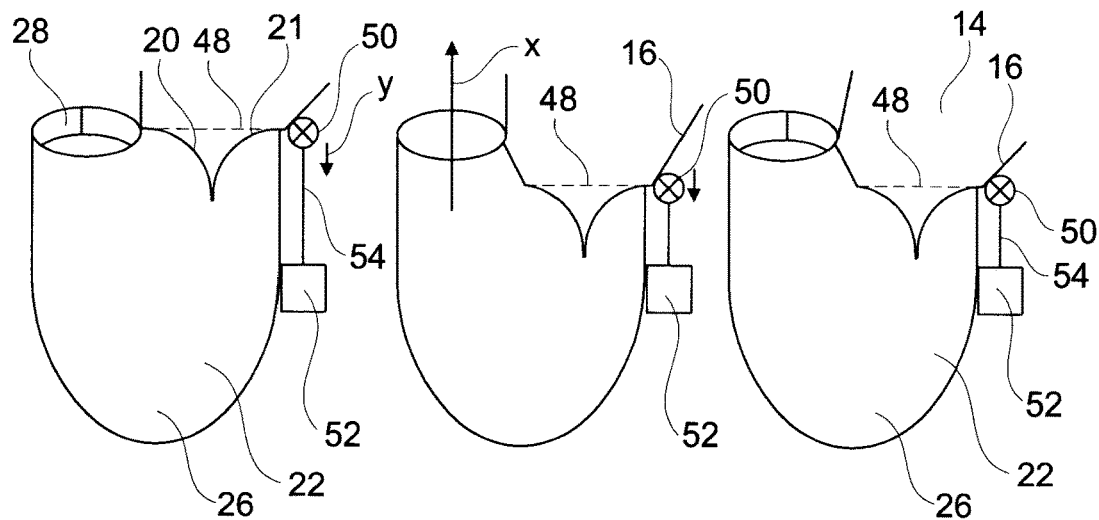
FIGS. 5a-c, 6a-c, 7a-c, 8a-c and 9 are schematic illustrations depict schematic how the here presented invention may augment the mitral valve movement utilizing different embodiments.

FIG. 5 is a schematic view of an embodiment of a medical device for cardiac assist when inserted in the heart 1. Some embodiments, as the present device, has two anchor units. A first anchor unit 50, is located in the CS 8 and/or the GCV 12. The second anchor unit 52 is located remote from the first anchor unit. The second anchor unit 52 is for instance arranged inside a side branch of the vein system on the LV wall 22. The two anchors 50, 52 are in communication with each other. They are for instance, as illustrated, connected by means of a pulling and pushing unit 54 that can move the two anchors relative to each other. The figure depicts, as in FIG. 3, the movements in systole of the mitral valve plane 48 in relation to the LV apex 26, the GCV 12 (and CS) the MV anterior 20 and posterior 21 leaflets, the MV annulus 18, the aortic valve 28, the LA wall 16 and the LA cavity 14 during an augmented or assisted heart beat. The pulling and pushing unit 54 forces, powered by a power unit (not shown), such as a remote or external power unit, the two anchors closer to each other, and is thereby augmenting the force and extent of the downwards movement of the mitral valve 19. The left ventricular pump action is assisted. The large arrow (x) show the direction of the blood flow and the small arrow (y) the direction of MV plane, the GCV and the CS. In the cardiac cycle, the following moments are shown in FIG. 5: a) is just before systole, b) during systole and c) end of systole.

Figures 6A, 6B, 6C:
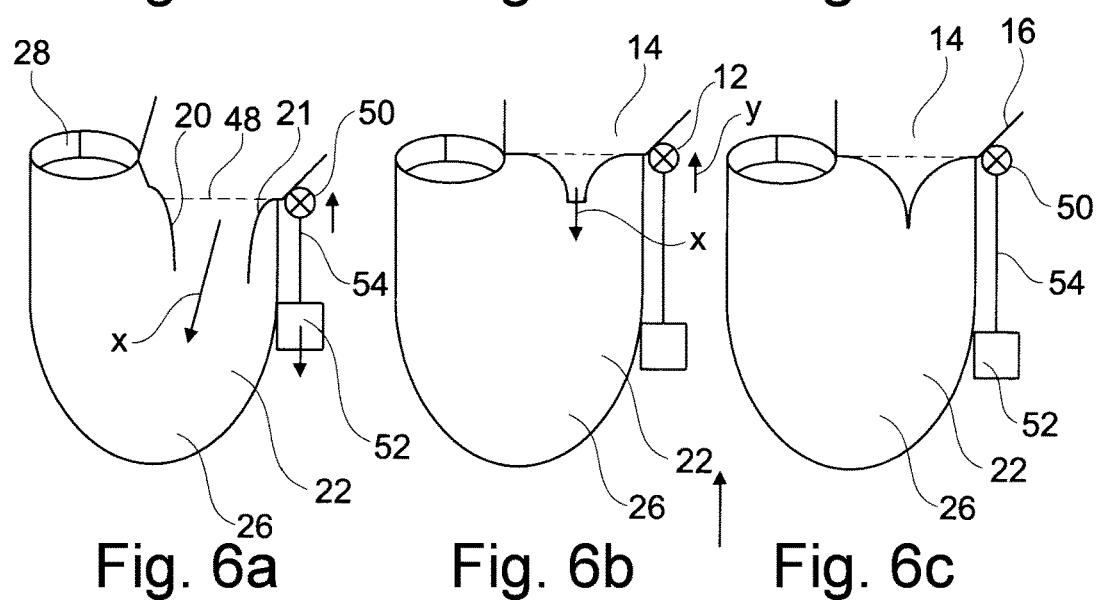

FIG. 6 is a schematic view of one embodiment of the invention when inserted in the heart 1. The two anchors, 50 is located in the CS 8 or the GCV 12, the other, 52 is located inside a side branch of the vein system on the LV wall 22. The two anchors are connected by means pulling and pushing unit 54 that can move the two anchors relative to each other. The figure depict as in FIG. 4 the movements in diastole of the mitral valve plane 48 in relation to the LV apex 26, the GCV 12 (and CS) the MV anterior 20 and posterior 21 leaflets, the MV annulus 18, the aortic valve 28, the LA wall 16 and the LA cavity 14 during an augmented heart beat, the pulling and pushing unit 54 forces, powered by means of an remote or external power unit 84 (not shown) the two anchor units away from each other. As the anchors are fixed to the tissue where they are anchored, the tissue structure is moved with the anchor unit(s). The anchor unit(s) are thereby augmenting the force and extent of the upwards movement of the mitral valve 19 towards the LA. Thereby the device is enhancing the diastolic filling of the LV before the next heart beat. Hence, even during diastole the cardiac assist is provided. The large arrow x shows the direction of the blood flow and the small arrow y the direction of MV plane 48, the GCV and the CS. In the cardiac cycle, the following moments are shown in FIG. 6: a) early diastole, b) late diastole and c) end of diastole, the mitral valve is now closed and ready for the next move downwards.

A prototype of the invention was built, using a linear accelerator and a computer. The computer allowed action in synchrony with an electrocardiogram. The prototype was tested in an animal experiment. The chest of a 60 kilogram pig was opened between the ribs. A rod from the linear accelerator was attached to the mitral valve annulus from the outside of the heart. The heart function was depressed by means of drugs. After activating the device an increase in arterial blood pressure and cardiac output was observed.

Figures 7A, 7B, 7C:
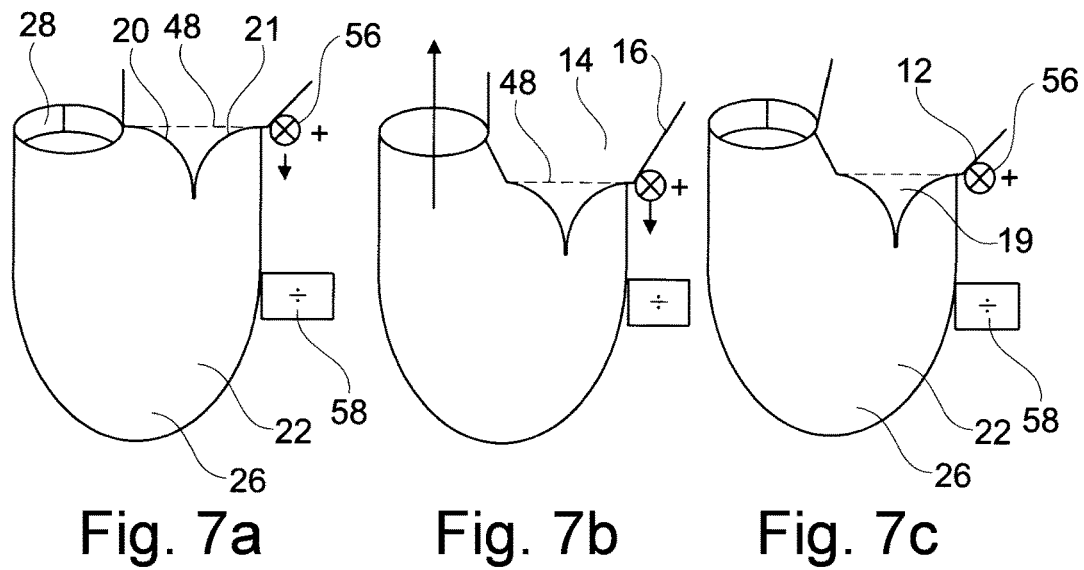

FIG. 7 is a schematic view of another embodiment of the invention when inserted in the heart 1. The device has two anchor units. A first anchor unit 56, is located in the CS 8 and/or the GCV 12. The second, remote, anchor unit 58, is located inside a side branch of the vein system on the LV wall 22 or is attached to the LV outer wall. Here, the two anchors are magnets. Preferably they are provided in form of electromagnets, but one or the other magnetic anchoring unit may also be a traditional permanent magnet. The electromagnetic magnets are arranged to change polarity, synchronized with the heart cycle in order to change between pulling towards each other and pushing away from each other. There are no physical connecting units between the magnetic anchoring units. The anchoring units are only in magnetic connection. When the anchoring units have different polarity they move the two anchors closer to each other and correspondingly when the polarity is equal they move the two anchors away from each other. FIG. 7 depicts, as in FIG. 3, the movements in systole of the mitral valve plane 48 in relation to the LV apex 26, the GCV 12 (and CS) the MV anterior 20 and posterior 21 leaflets, the MV annulus 18, the aortic valve 28, the LA wall 16 and the LA cavity 14 during an augmented heart beat. The magnetic anchors 56 and 58 attract each other and forces by means of magnetic power the two anchors closer to each other, and is thereby augmenting the force and extent of the downwards movement of the mitral valve 19. The large arrow shows the direction of the blood flow and the small arrow the direction of MV plane, the GCV and the CS and the magnet 56. In the cardiac cycle, the following moments are shown in FIG. 7: a) is just before systole, b) during systole and c) end of systole.

Figures 8A, 8B, 8C:
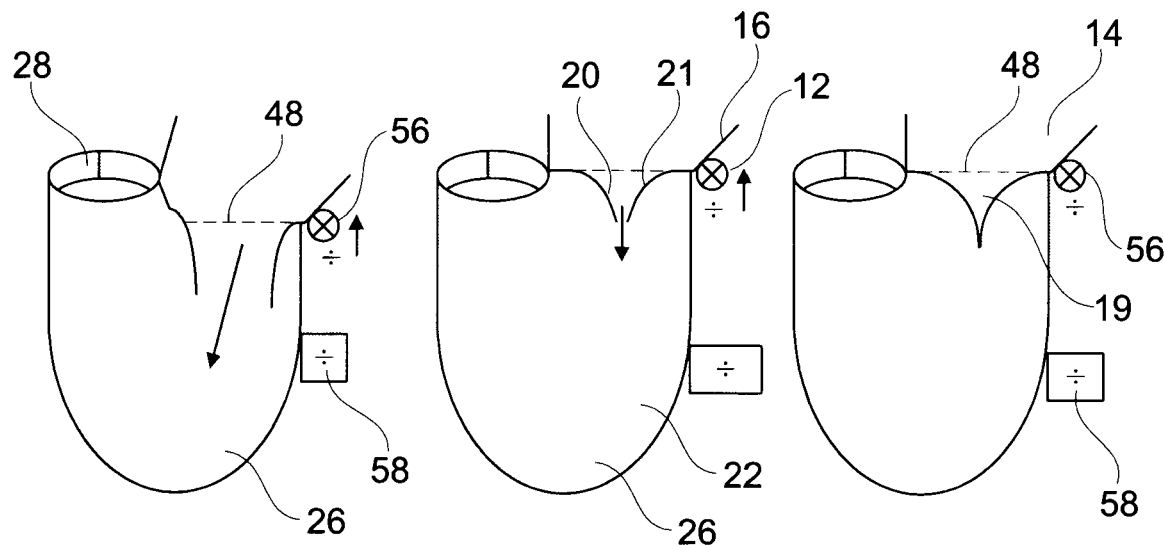

FIG. 8 is a schematic view of the same embodiment as in FIG. 7 in diastole. The first anchor unit 56 is located in the CS 8 and/or the GCV 12. The second anchor unit 58 is located remote from the first anchor unit 56. Here, the second anchor unit is located inside a side branch of the vein system on the LV wall 22. Alternatively, or in addition, it may be attached to the LV outer wall. The two anchors are magnets, preferably electromagnets, but one or the other may also be a traditional permanent magnet. The electromagnetic magnets may change polarity synchronized with the heart cycle in order to change between pulling towards each other and pushing away from each other. There are no physical connecting units. When the anchoring units have different polarity they move the two anchors closer to each other and correspondingly when the polarity is equal they move the two anchors away from each other. FIG. 8 depicts, as in FIG. 4, the movements in diastole of the mitral valve plane 48 in relation to the LV apex 26, the GCV 12 (and CS) the MV anterior 20 and posterior 21 leaflets, the MV annulus 18, the aortic valve 28, the LA wall 16 and the LA cavity 14 during an augmented heart beat. The magnetic anchors 56 and 58 now have equal polarity (both negative or both positive) and push each other away and thus the two anchors are forced away from each other by means of magnetic power, and is thereby augmenting the force and extent of the upwards movement of the mitral valve 19. The large arrow shows the direction of the blood flow and the small arrow the direction of MV plane and the magnet 56, the GCV and the CS. In the cardiac cycle, the following moments are shown in FIG. 8: a) early diastole, b) late diastole and c) end of diastole.

Figure 9:
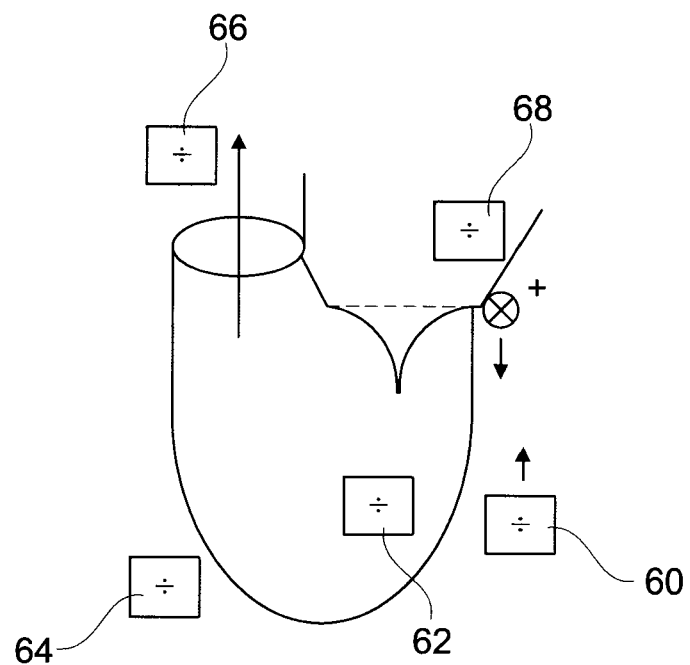

In FIG. 9 an alternate positioning of the second magnet anchor unit 58 is shown. The second anchor unit 58 can be electromagnetic or classic permanent magnetic. The second anchor 60 can be electromagnetic or classic permanent magnetic. When being permanent magnetic, the first magnetic anchor 56 is an electromagnetic unit with selectively activateable magnetic polarity. The second anchor 60 can be placed in different positions in the heart. However, positions outside the heart are also possible in certain embodiments. Location 61 indicates a position where the second anchor 60 is not attached to or in the heart. One such position is in the pericardium. Another position is in the pleura or under the skin. Possible attachment sites include the pericardium, the diaphragm. The spine or the thoracic cage (ribs and sternum) are also suitable sites for attachment of the second anchor 60. Positions 62, 64, 66, 68 indicate positions for the second magnet anchor 60 relative the heart. Position 62 is located in the left ventricle and position 64 is located in the right ventricle. Position 66 is located in the RA, preferably in the so called atrial septum between the RA and the LA. One good position is in the foramen ovale of the atrial septum where often an opening is present to the LA. In this embodiment, the second anchor unit may have the shape of a septal occluder and provide both septal leakage occlusion and allows for support of the cardiac function. Position 68 indicates a position in the LA, again a good attachment site would be the atrial septum, another good position in the LA would be the LA appendage (LAA, not shown). In this embodiment, the second anchor unit may have the shape of an LAA occluder and provides both LAA occlusion and allows for support of the cardiac function. These are only examples and a person skilled in the art may think of multiple variations that would work equally well for the purpose.

Figure 10A:
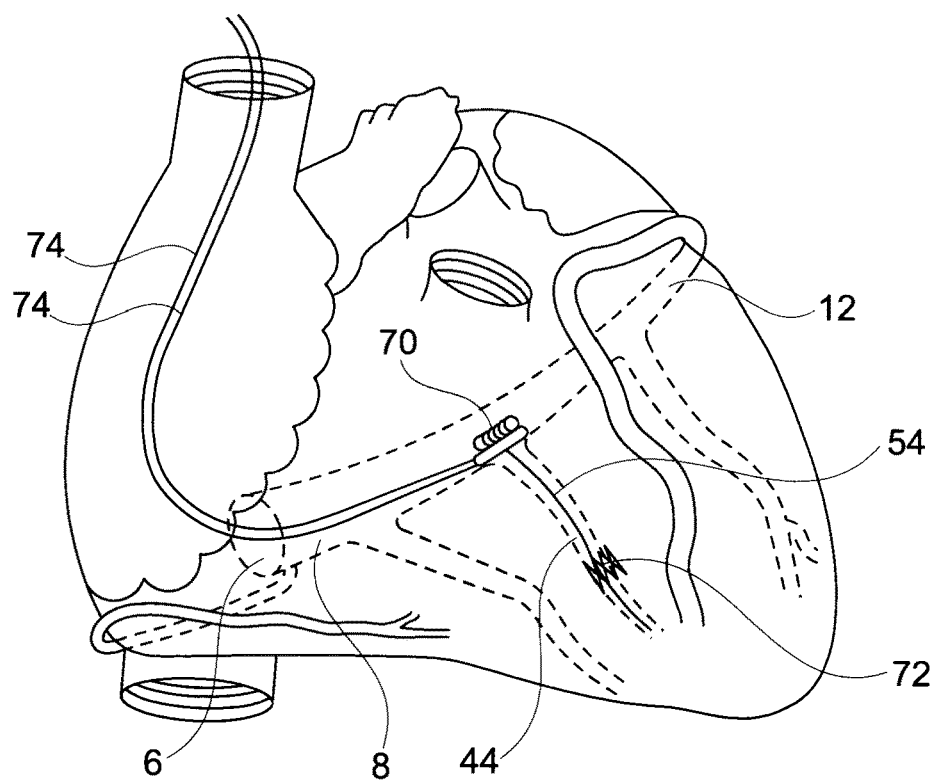
FIGS. 10a-b, 11a-b and 12a-b are schematic illustrations that describe different embodiments utilizing pulling and pushing forces in order to augment the mitral valve movement.

In FIG. 10a another embodiment is shown where the supporting or assist force is executed by means of a mini motor 70 integrated in the CS anchor and/or GCV anchor. MEMS (micro-electro-magnetical-systems) technology could be utilized for constructing such a motor. One or more second anchor units 72 are arranged in one or more side branches 44, to which the connecting unit 54 is attached, respectively.

Permanent magnets in embodiments may be conventional iron magnets. Alternatively, super magnets, like Neodymium rare earth magnets may be used to improve efficiency and/or reduce size of the units of the cardiac assist system, when comprising magnetic elements.

An anchor unit may for instance be provided in form of a stent. The stent serves as an anchor in a vessel. Such a stent could be a self expanding stent for instance made of a shape memory material, like a shape memory metal like superelastic Nitinol. The mini motor 70 could then be integrated in the stent structure (not shown). The stent could also be a stent made of a material or having a structure that has to be expanded by means of a balloon, for instance made of stainless steel or another metal suitable for the purpose. Alternatively, or in addition, an anchor unit is made with hooks that dig into the tissue made of similar materials, these are only examples and a person skilled in the art may think of multiple variations that would work equally well for the purpose when reading the present description. Thus, the motor 70 is attached to the vessel structure. This may be made with stent technology and/or by means of hooks that a person skilled in the art will find multiple solutions for. However, common for all these solutions is that they will be executed by means of catheter based techniques by means of puncture of a vessel, preferably a vein, through the skin.

Figure 10B:
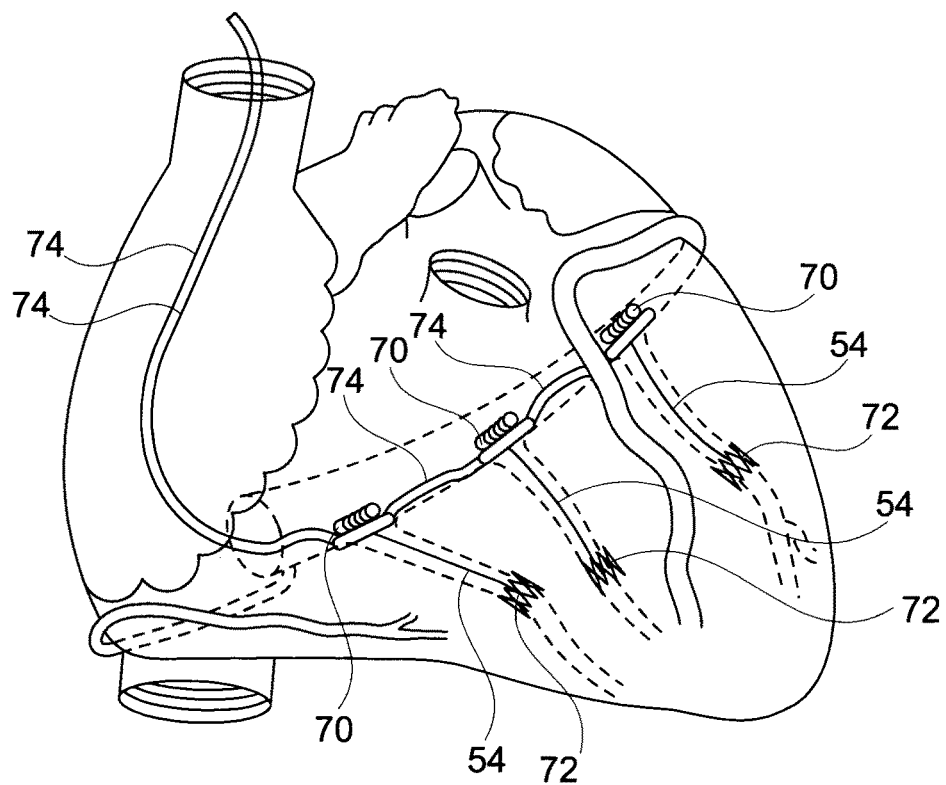

Multiple sets of motors 70, anchors 72 and connecting units 54 may be implanted simultaneously and connected to one or more energy sources 84 (not shown) as is described in FIG. 10b. Electrical power for the mini motors is provided from the remote energy source 84 by means of insulated cables 74.

Figure 11A:
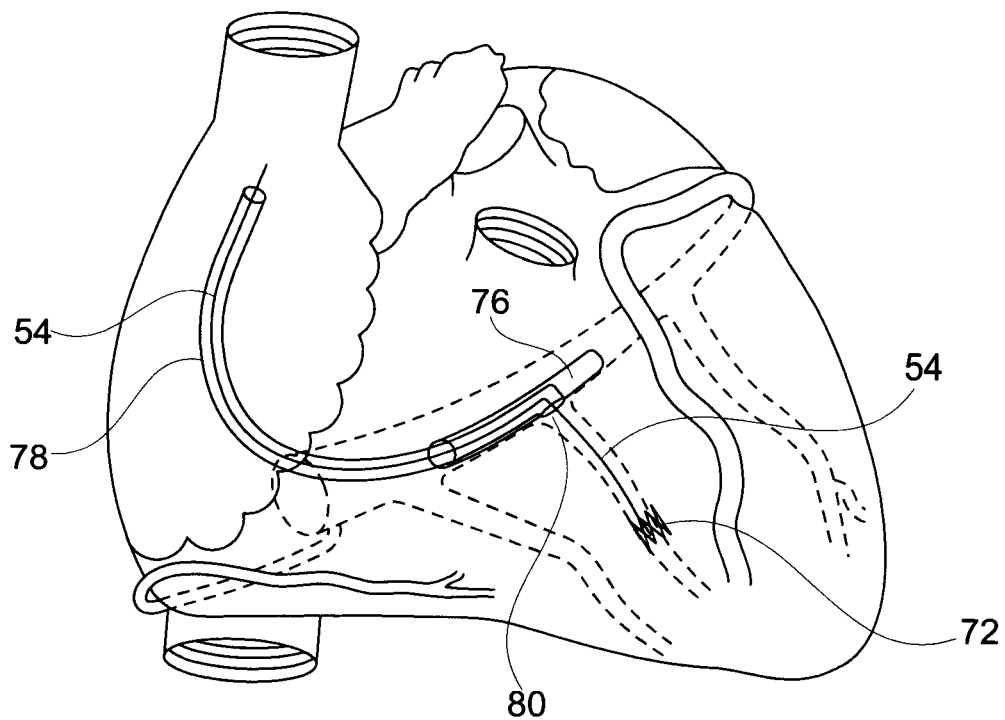
Figure 11B:
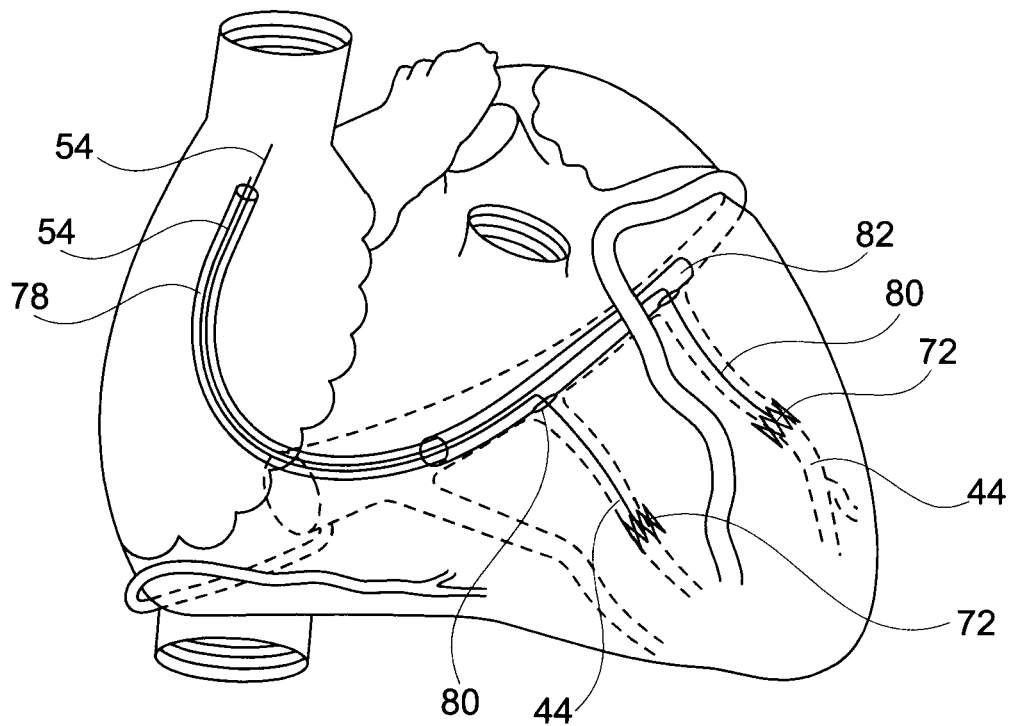

In still another embodiment shown in FIGS. 11a and 11b, the energy is mechanically transferred from the remote energy source 84 to the movement of the MV plane 48. The mechanical force may be provided through an extended connecting unit 54, like a wire or elongate flexible rod. The movement is transferred all the way from a mechanical actuator, e.g. at the remote energy source, to the anchor unit 72, through the CS or GCV anchor 76. The anchor unit 76 may have guiding units 80 for the connecting unit 54 in order to transfer the mechanical movement from the anchor 76 into the used side branch 44 of the vein system. A guiding sheath 78 may be fixated in the anchor 76 and in the energy source 84 in such a way that when pulling in the connecting unit 54 inside by the mechanical actuator, e.g. at the energy source, relatively to the guiding sheath 78 the distance between the anchors 72 and 76 will shorten. Correspondingly, when pushing the connecting unit inside the remote energy source, the distance between the two anchors 72 and 76 increases. The guiding unit may also be a mechanical unit that transfers a longitudinal (or rotational movement, see below) into a movement in a perpendicular direction of the unit 54. Thus the reciprocating up and down cardiac assist movement of the MV plane 48 is provided.

Turning to FIG. 11b, an embodiment of the type described with reference to FIG. 11a is shown, except that the CS or GCV anchor 82 is designed for more than one anchor in side branches 44. In this manner, advantageous improved efficiency of the cardiac assist device may be provided. Geometric distribution of the supporting force may be provided that is advantageous for the cardiac structures in a long term use of the device.

Figure 12A:
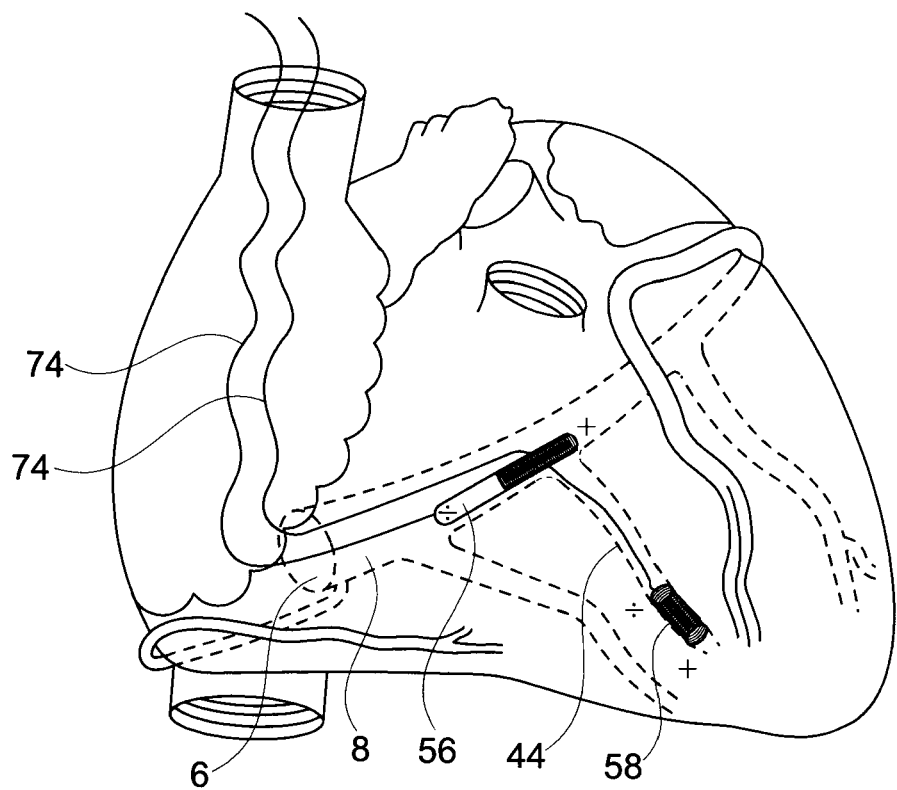
Figure 12B:
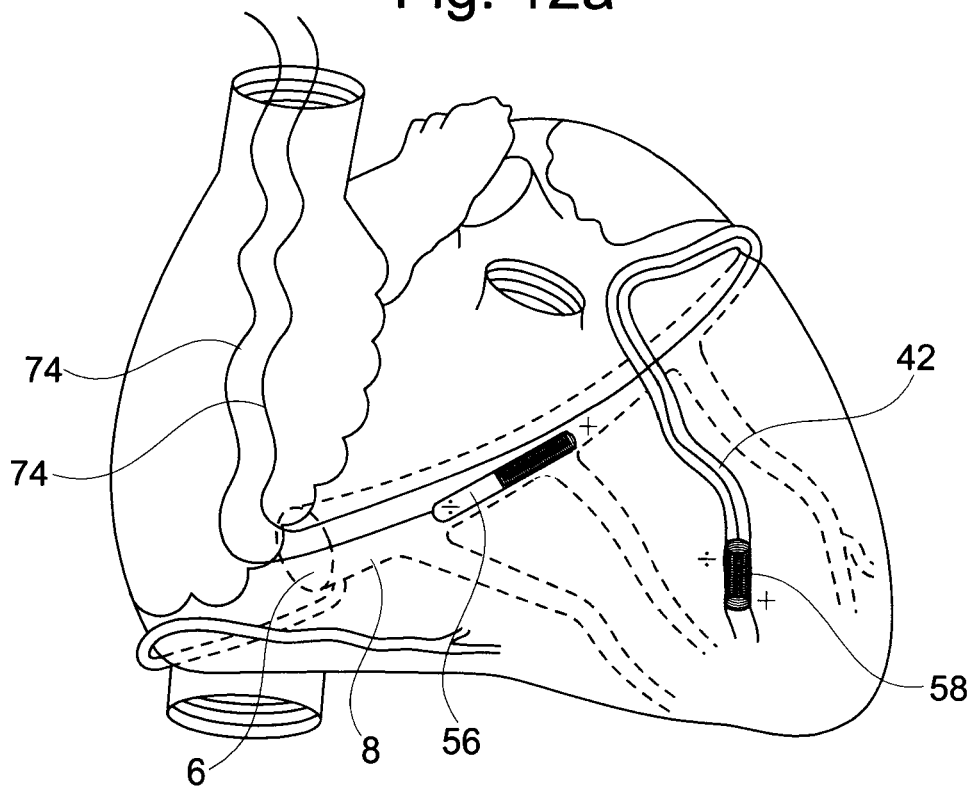

The FIGS. 12a and 12b show examples of configurations described in FIGS. 7, 8 and 9 where electromagnets are used as anchors. Different combinations of electromagnets and classical permanent magnets will not be described in separate figures as they would be apparent for the skilled person when reading the present application. In FIG. 12a the first anchor is located in a side branch 44 from the CS or the GCV and in FIG. 12b in the anterior inter-ventricular vein (AIV).

Still another embodiment of the innovation is depicted in the FIGS. 13, 14, 15 and 16. Instead of pulling and pushing the extension 54, the mechanical force is instead transferred by means of rotation of the extension unit 54. Now the distal anchor 73 of the device is not located in a side branch. Instead, it is placed in the distal GCV 12 itself or in its continuation, the anterior inter-ventricular vein 42. This embodiment takes advantage of the fact that the three dimensional shape of the CS and the GCV represents a loop from behind the heart, around the left angle of the heart to its front surface. The loop is substantially oriented in the mitral valve plane 48, see e.g. FIG. 2b. The extension unit 54 is an elongate loop shaped unit, distally ending at the distal anchor unit 73, where it is attached to the distal anchor unit 73, see e.g. FIGS. 15a-c. Hence, the loop shaped extension unit 54 may be suitably actuated to move the CS and/or the GCV in direction to and/or from the LV apex 26. As the MV is connected by cardiac tissue to the CS and GCV, a movement of the extension unit 54 is transferred to the MV plane 48.

Figure 13:
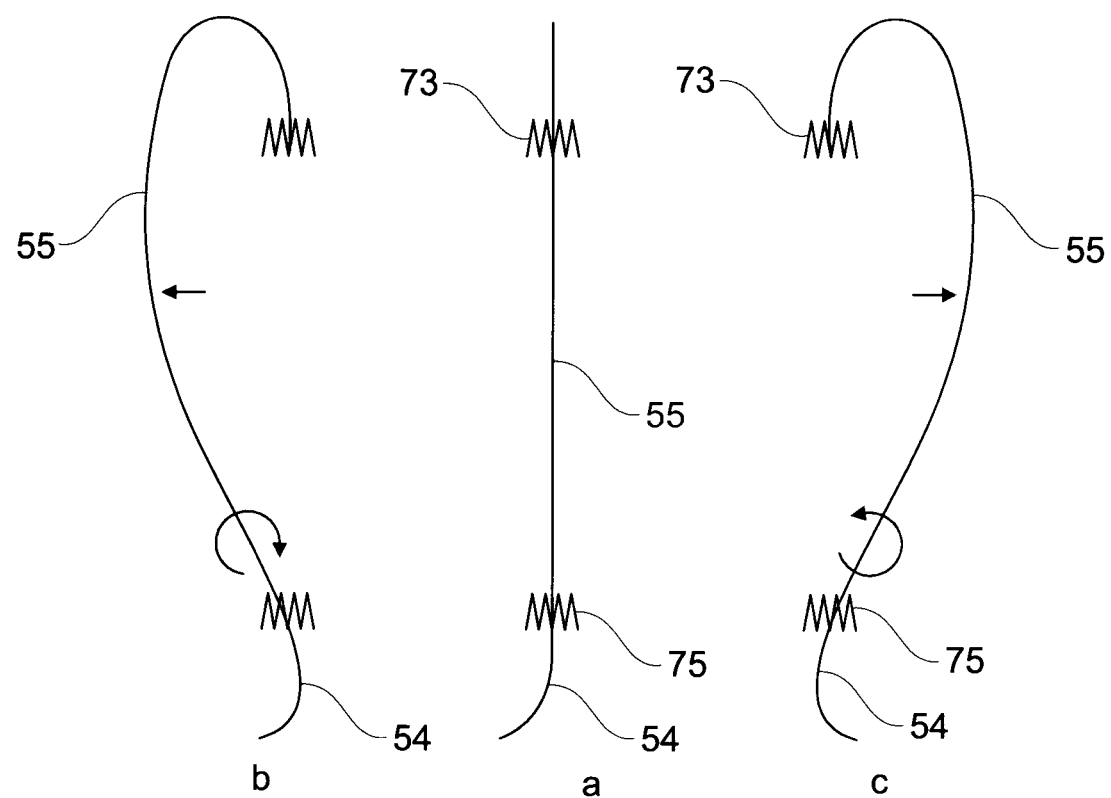
FIGS. 13, 14, 15a-e and 16a-b are schematic illustrations that describe different embodiments utilizing rotation forces in order to augment the mitral valve movement.

In FIG. 13 the part of the extension 54 that is located inside the CS and the GCV, here numbered with 55 is depicted. The device has different operative positions, as shown in FIGS. 13a-c. In the neutral position, depicted in FIG. 13a, we have a perpendicular view of the loop that will appear as a straight line from that angle. Compare also the view in FIG. 15a.

A distal anchor unit 73 is located at the front of the heart. Most preferable the distal anchor unit 73 is made of a stent design. A second anchor 75 is arranged proximally of the distal anchor 73 in the GCV or preferably in the CS as close to the ostium 6 (FIG. 1) as possible. The second anchor is preferably made of a stent design. Additional anchors 77 may be located for support anywhere between the distal end anchor 73 and the proximal end anchor 75, see e.g. FIG. 14. The additional anchors are preferably made of a stent design.

The extension unit 54 is proximally connected to a mechanical actuator that controllably rotates the extension unit 54 synchronized with the cardiac cycle. In the embodiment, the extension unit 54 is proximally connected to the remote energy source 84. However, other arrangements and locations of the mechanical actuator providing the rotational movement of the elongate extension unit 54 may be provided in other embodiments. The mechanical actuator may for instance be arranged intra-cardiac.

While rotating the extension unit 54 clockwise (seen from the mechanical actuator, here the remote energy source 84 end), as shown in position b in FIG. 13, the loop 55 flexes towards the LA 14, moving the CS and the GCV also in this direction. Since the CS and the GCV are so closely related to the MV, such a backwards movements in relation to the LV apex will augment the normal upwards movement of the MV in diastole if the clockwise rotation is done in diastole.

In analogy to this, a counter-clockwise rotation in systole will augment the downwards movement of the closed MV (piston) in systole, as depicted in FIG. 13, position c).

Figure 14:
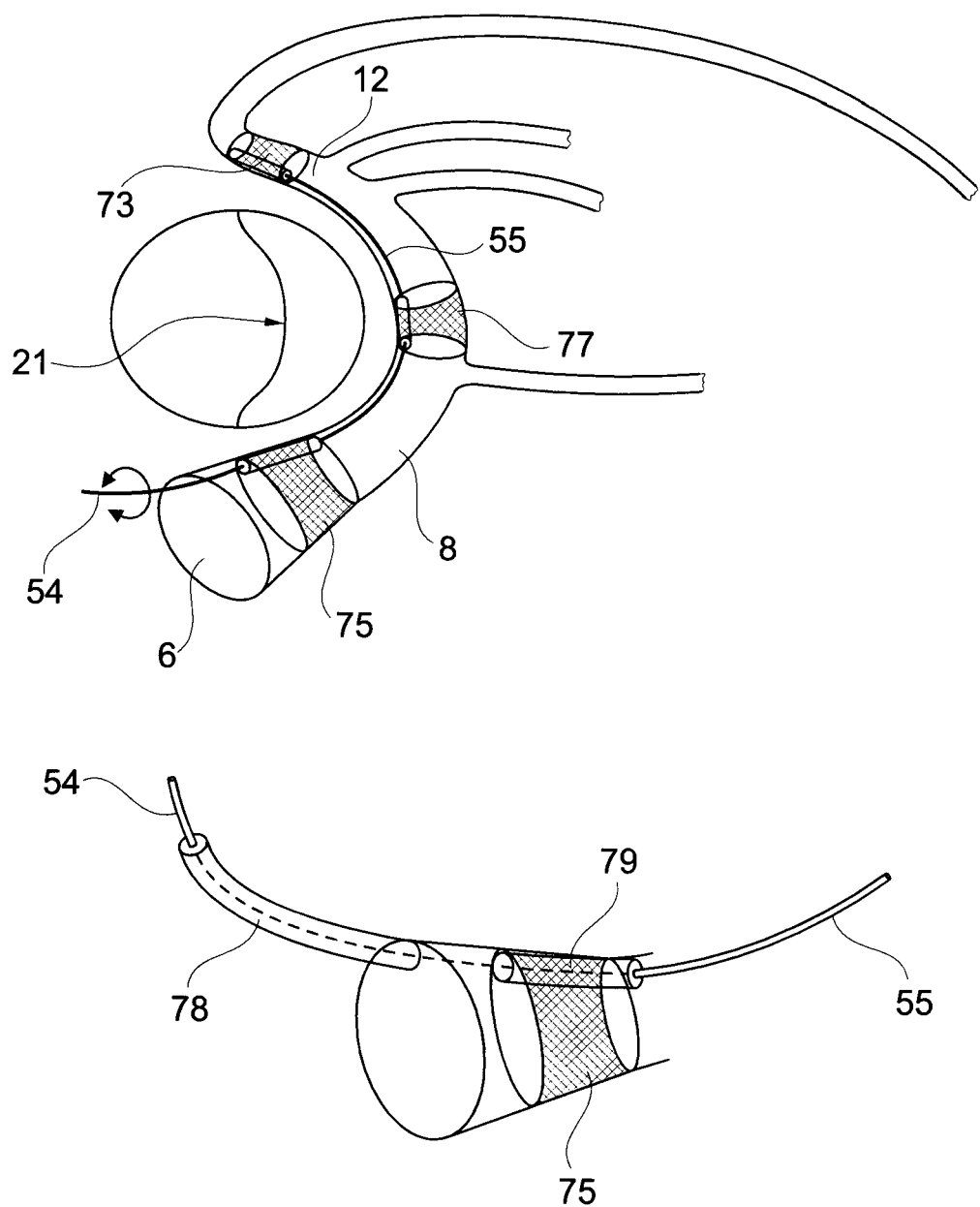

In FIG. 14 it is also illustrated that there in addition may be a retention unit 79 that locks the extension unit 54 longitudinally to stay at the location of the proximal anchor unit 75. The retention unit may be a tube or loops located in the anchors allowing the extension 54 to rotate, but will prohibit axial movements in order to prevent dislocation of the extension units 54 and 55. Extension units 54 and 55 may be in one integral piece or have different segments that are articulated (not shown). The number of segments and articulation may be suitably chosen in order to design stiffness or flexibility necessary to accommodate the device in place while still being functional.

FIG. 15 illustrates in more detail the embodiment taking advantage if rotating a loop in an anatomical environment. FIG. 15a depicts the neutral position. In FIG. 15b the extension units 54 and 55 are rotated clockwise. Now the loop of 55, the CS, the GCV and the mitral valve move up towards the LA in diastole. In FIG. 15c the extension units 54 and 55 are rotated counter-clockwise and the loop of 55, the CS, the GCV and the mitral valve moves down towards the LV apex in systole.

The direction of the MV plane movement, here related to the rotation, is controlled, e.g. based on ECG detection, and in synchronisation with the cardiac cycle. A control unit operatively connected to implement the control is provided, as described in an example below. The control unit may be implemented in the remote energy source unit 84.

Figure 15A:
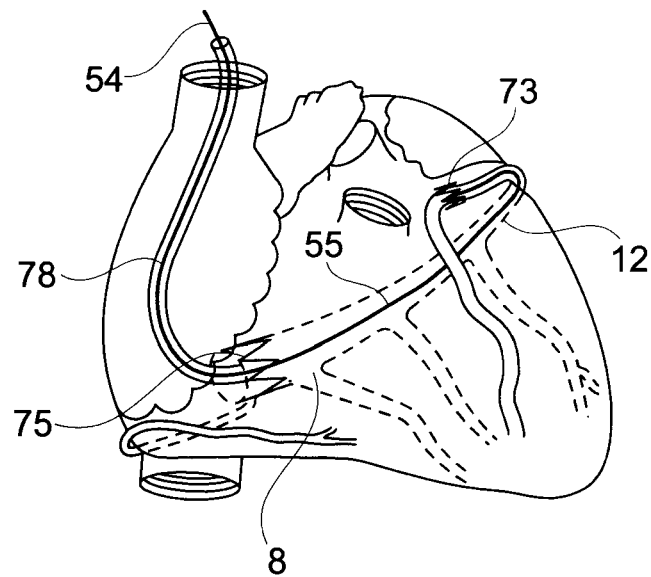
Figure 15B:
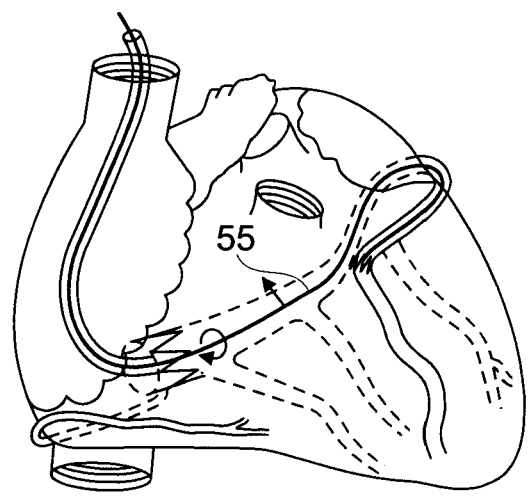
Figure 15C:
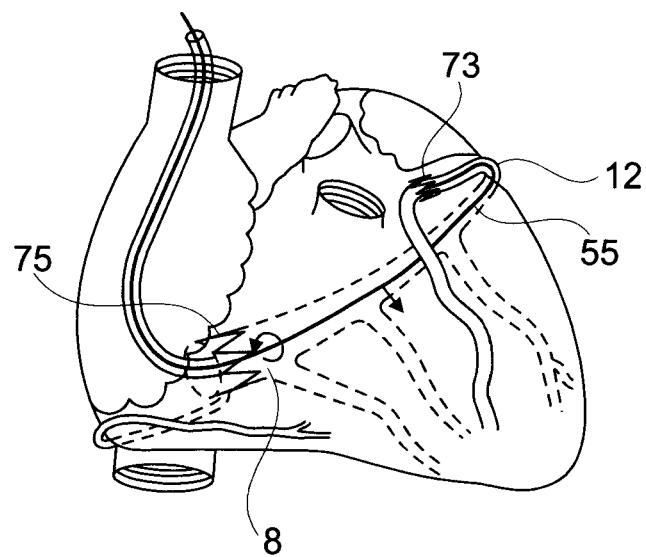
Figure 15D:
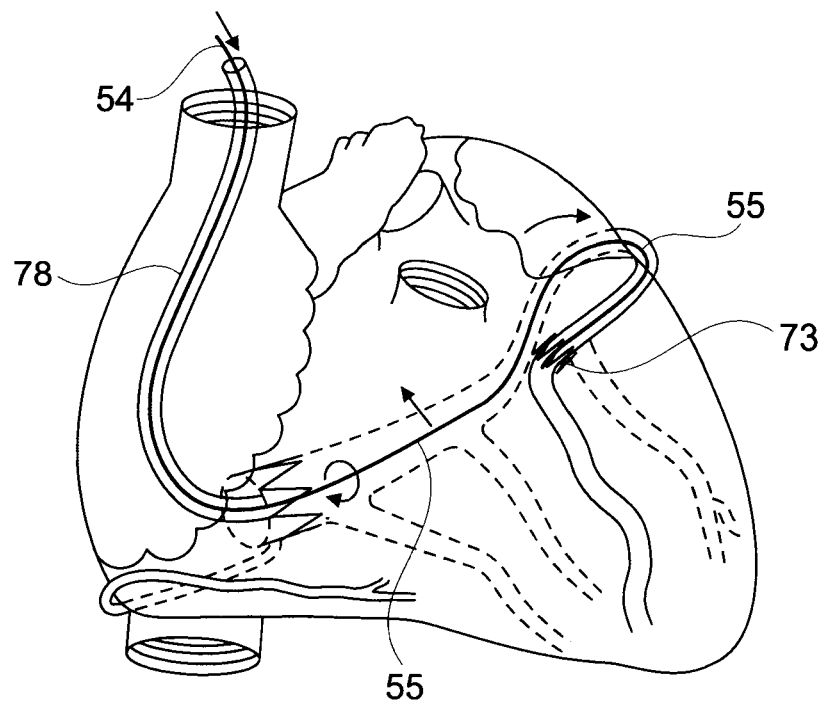
Figure 15E:
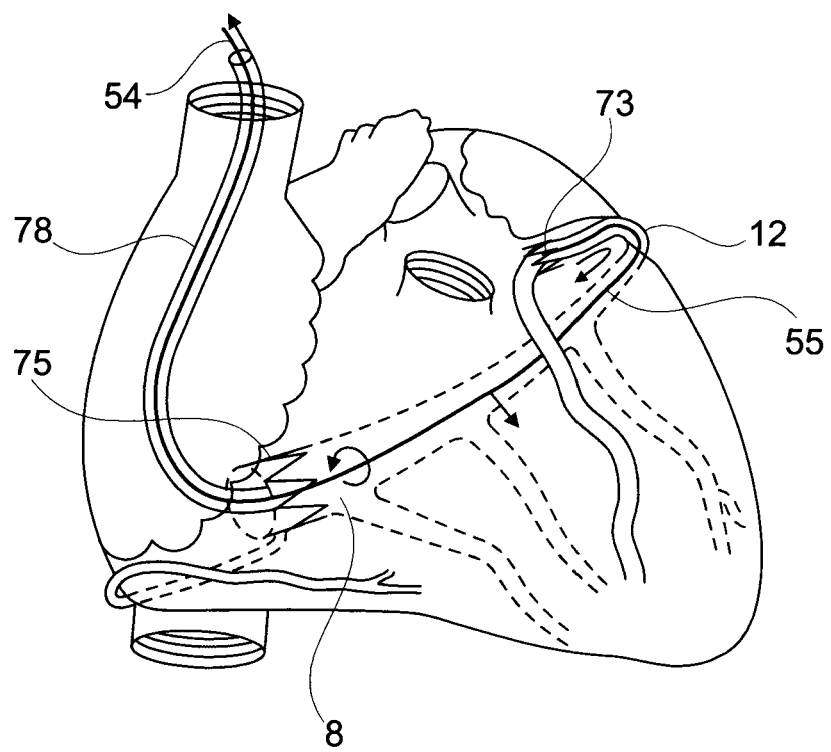

Further, in another embodiment, in addition to the rotational movement, a longitudinal movement of the extension unit 54 may be added. By pulling the extension unit 54, attached to the distal anchor 73, relative to the sheath 78, that now is fixed to the proximal anchor 75, the distance between anchors 73 and 75 may be reduced. This additional transversal controlled movement may in some embodiments include moving the lateral LV in the heart in a reciprocating movement during systole towards an inter-ventricular septum of the heart and during diastole away from an inter-ventricular septum for assisting the pump action of the heart along the short axis of a LV of a heart. In FIG. 15d it is illustrated that in diastole the extension unit 54 is moved distally relative to the sheath 78, in addition to the clockwise rotation. The length of the connecting extension unit portion between the proximal and the distal anchor is thus extended. Thus, the outwards movement of the lateral LV wall is augmented relative to the intra-ventricular septum. In Systole on the other hand, as shown in FIG. 15e, the extension unit 54 is moved proximally relative to the sheath 78, the distal anchor 73 is pulled closer to the proximal anchor 75, in addition to the counterclockwise rotation. The length of the connecting extension unit portion between the proximal and the distal anchor is thus shortened. Thus, the inwards movement of the lateral LV wall is augmented relative to the intra-ventricular septum. The direction of the LV lateral wall movement, here related to the pulling and pushing in addition to the rotation, is controlled, e.g. based on ECG detection, and in synchronisation with the cardiac cycle. A control unit operatively connected to implement the control is provided, as described in an example below. The control unit may be implemented in the remote energy source unit 84. The coronary sinus implant of embodiments may thus be adjusted during at least a portion of a single cardiac cycle. Adjustment is made instantaneously upon actuation. In alternative embodiments, the short axis support actuation may be made based on other units and actuating principles, including electric or magnetic actuators, etc. In addition, the medical device may have a plurality of sections which are individually adjustable in length by an actuating unit, controlled by said control unit arranged to controllably change said shape of said sections individually. For instance, embodiments of the device may comprise anchoring units between each of said plurality of sections, wherein the length of the sections is adjustable e.g. by pulling together or pushing apart distal and proximal anchoring units of a section.

Figure 16A:
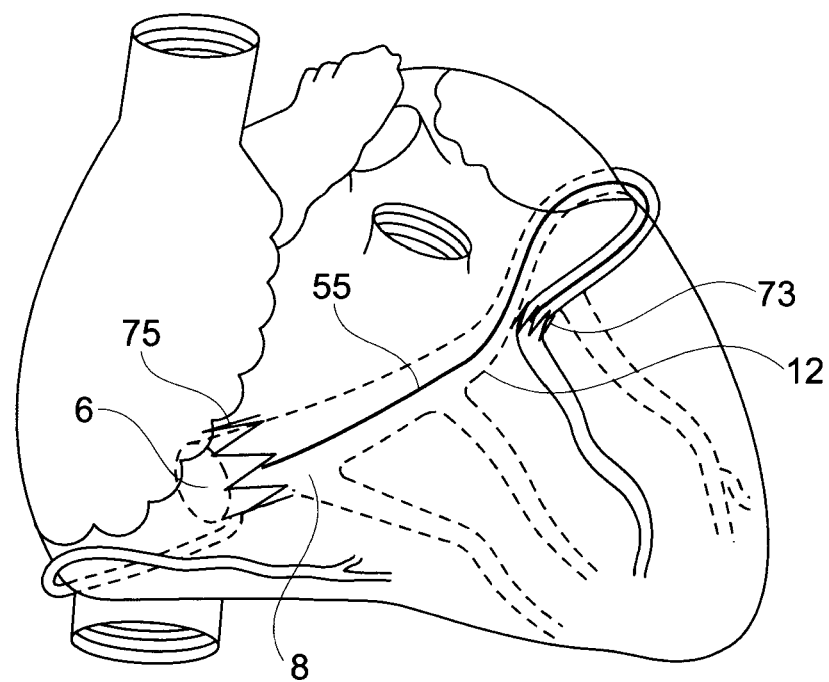
Figure 16B:
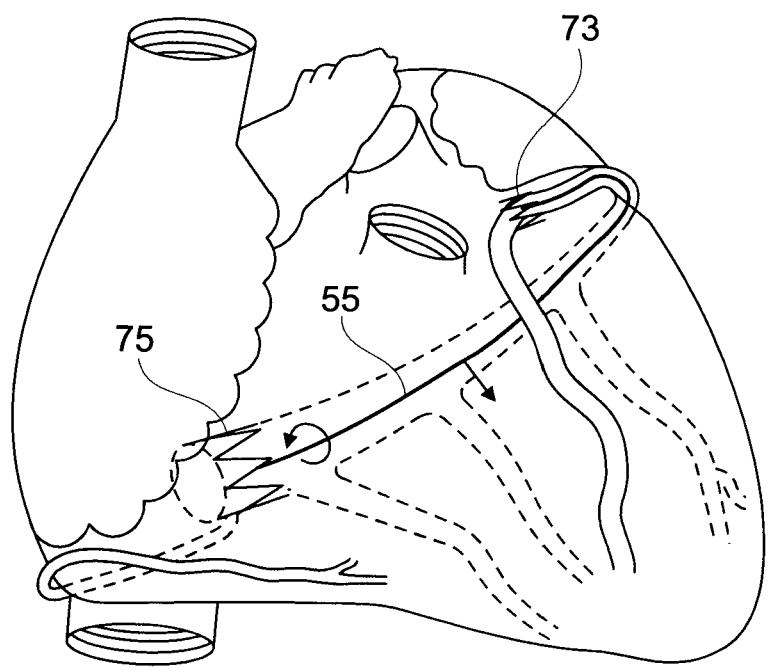

In another embodiment the inherent force of a spring is utilized shown in FIGS. 16a and 16b. Here the extension unit 55 is inserted and detached in the CS and the GCV or in the AIV. Preferably the extension 55 in this embodiment has fix attachments to the distal and proximal anchor units 73, 75. The cardiac assist device is provided as a resilient unit. In this embodiment, the cardiac assist device is provided in a relaxed position in the MV plane up position. The relaxed position of the unit is spring loaded against a MV plane down position. The loop 55 of the extension unit 54 has as a default preferred state the relaxed position. The extension unit thus forces the CS, the GCV and the mitral valve to move up towards the LA, both in diastole and in systole, namely against the spring load force. The inherent spring load force is chosen to be less than the MV plane downward force provided by the LV muscle. Thus, in systole, the cardiac muscle force of the LV will be stronger than the inherent spring force of the extension 55 and bring the loop down towards the LV apex in systole. Such a device thus assists during the diastole when it increases the LV diastolic filling by forcing the open MV up against the blood stream further in the direction of the LA. On the other hand, the resilient unit may have a relaxed position in a lower MV plane position spring loaded against a MV plane up position, such that the cardiac relaxation force of the LV brings the loop to the up position, and the resilient unit assists during the systole by assisting the LV systolic contraction by forcing the closed MV down towards the LV apex.

Such non-powered devices might be made of Nitinol, a memory shape metal or stainless steel or any other suitable material, preferably metal. A control unit or remote energy unit 84 are omitted in these particular embodiments. The action may be delayed by integrating resorbable material, in the device in order to delay its action and allow the device to grow in before its action is initiated while the resorbable material disappears. Such material could be for instance be PLLA, Polyvinyl or Polylactid or other resorbable materials.

Alternatively, or in addition, the cardiac assist system may be provided as a bistable system. Here, the diastolic up position and the systolic down position of the MV plane may be provided as equilibrium states of the system. Energy is either provided from the external energy, or from the LV muscle source to initiate the system to move between the two stable positions. These embodiments may be more energy efficient than others.

In embodiments the cardiac assist device has a control unit and a sensor for measuring physiological parameters related to the cardiac cycle activity providing a sensor signal. The sensor signal is provided to the control unit which controls the displacement unit to provide the movement by energy from an energy source and based on the sensor signal. The cardiac assist device operation is thus controlled in synchronicity with the heart action. The sensor may be an ECG electrode or in addition or alternatively be based on detecting other physiological parameters related to the cardiac activity, such as a blood pressure wave, blood flow patterns, or acoustic signals of the cardiac activity.

Figure 17:
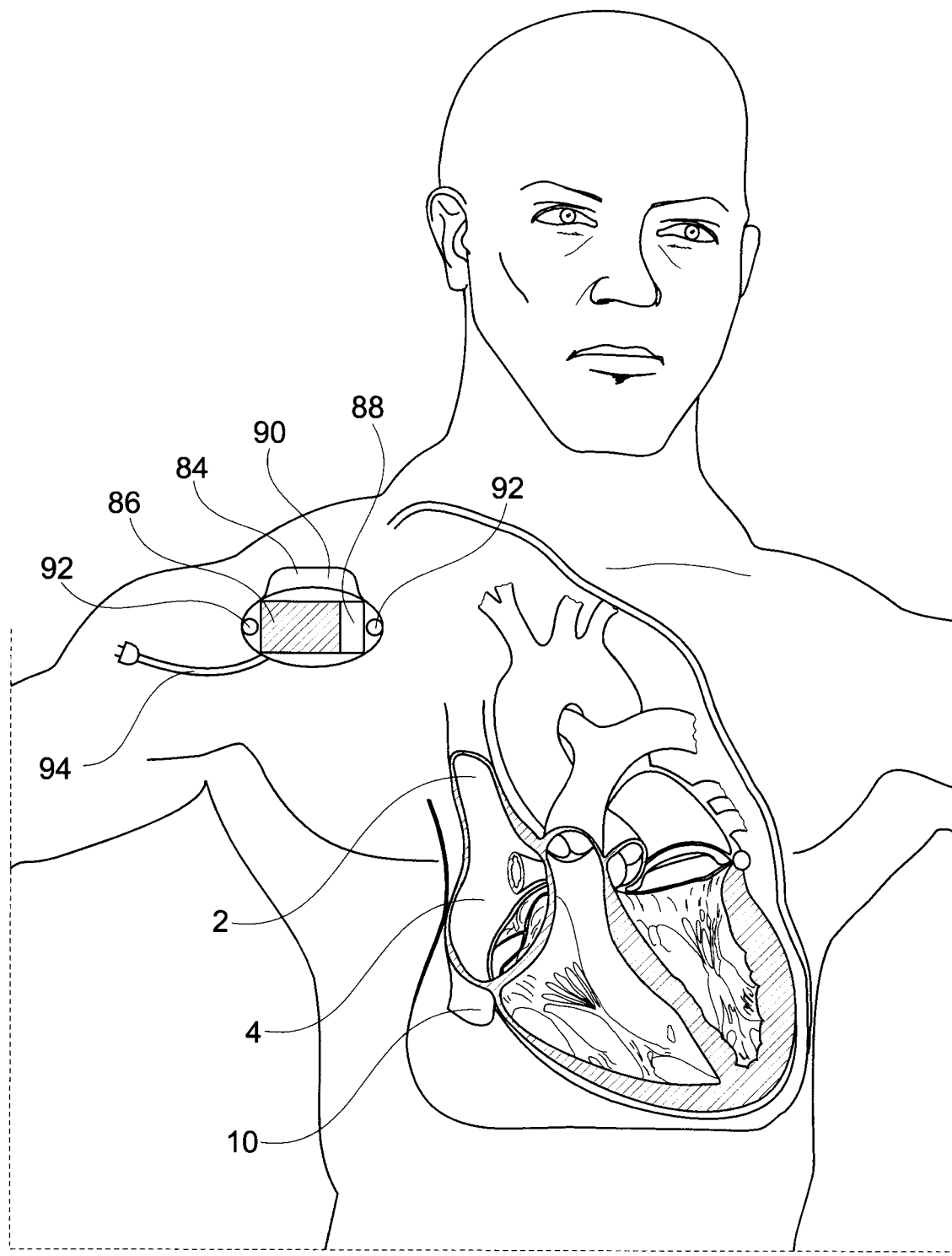
FIG. 17 is a schematic illustration that shows a remote energy source.

A remote energy source 84 as comprised in some embodiments, is shown in FIG. 17. It has a battery section 86 and a computing section 88 containing computer algorithms and chips. The computer section 88 has receiving electrodes or surfaces 92 connected, which are able to detect an Electrocardiogram (ECG) signal. Based on the ECG signal, the cardiac assist device operation is in embodiments controlled in synchronicity with the heart action.

Such synchronicity may in addition or alternatively be established by means of detecting other physiological parameters related to the cardiac activity. Such parameters include a blood pressure wave, blood flow patterns, or acoustic signals of the cardiac activity.

Alternatively, or in addition, the assisted movement of the cardiac assist device may be controlled according to a set sequence of assisted movements of the MV plane that mimics the natural cardiac cycle to optimize the cardiac assist function. Frequency, speed, and duration of different pause times of the assisted movement may be set in the sequence to mimic a natural or desired movement. The different parameters, such as pause time duration of the movement, may vary over any time interval, and may be set to vary according to a repeating program. The sequence may be programmed into the computing section/control unit 88 which controls the force generating unit. The force generating unit may then provide the assisted movement according to the set sequence. Energy from an energy source 84 may thus be controllably provided to the force generating unit according to the set sequence for providing the assisted movement.

Alternatively, or in addition, the medical device may be incorporated into an artificial pacemaker system controlling or assisting the natural cardiac muscle function. For instance the assisted movement of the cardiac assist device may be controlled from a processing unit of a pacemaker. The pacemaker including the processing unit may be implanted in a patient. The pacemaker triggers heart muscle activity in a per-se known manner, e.g. via leads connected to the cardiac tissue for artificially triggering the cardiac activity. Triggering of the assisted movement of the cardiac assist device may be controlled may be based on the electrical triggering of the cardiac activity by the artificial pacemaker system, which is already synchronized with the cardiac cycle. Preferably a time delay is provided from triggering electrical triggering of the heart muscle activity to the triggering/activation of the assisted movement of the cardiac assist device during a heart cycle. The amount of the time delay may be optimized, depending on the transfer time of electrically triggering the heart muscle activity and the resulting pump function of the heart caused by the controlled heart muscle contraction.

The remote energy source 84 may have a mechanical section 90, where rotational or linear motion may be transferred to extension unit 54. Rotational movement may be transferred directly from an electrical motor, or geared down in revolutions by a gear-box. Rotational energy from an electrical motor may be converted to linear movement, enabling pulling and pushing force to a wire connecting unit 54 that is extending all the way to the distal anchor position. Alternatively, or in addition, the mechanical section 90 may contain other actuators. For instance one or more strong electromagnets may be provided in an actuator that alternately are able to provide pulling and pushing force to wire connecting unit 54 that is extending all the way to the distal anchor position.

Further, the pulling and pushing force from the remote energy source 84 may also be achieved by means of a linear accelerator in the mechanical section 90. Alternatively, or in addition, the mechanical section 90 contains an actuator providing pulling and pushing force to extension unit 73, e.g. a wire or elongate flexible rod of carbon fibre, that is extending all the way to the distal anchor position by means of electrically alternately cooling and warming a Nitinol actuator as commercially available from MIGA Motor Company, Modern Motion, www.migamotors.com. Finally, in other embodiments, the remote energy source is without a significant mechanical section, instead computer chips are distributing electricity from the battery according to the physiological cardiac cycle related signal, e.g. ECG signal, either to electromagnets in one or more of the anchor units of the implanted cardiac assist device or to mini-motors or linear actuators in a heart chamber or on the heart surface.

The remote energy source may have a rechargeable battery that is charged by means of a wire 94 penetrating the skin and when charging the battery connected to a charging device externally (not shown). Charging might also be done wireless through the skin, e.g. by means of electromagnetic coils transferring energy inductively. The skilled person in the art may alter and design such charging according to specific requirements and available actual technology.

Figure 18:
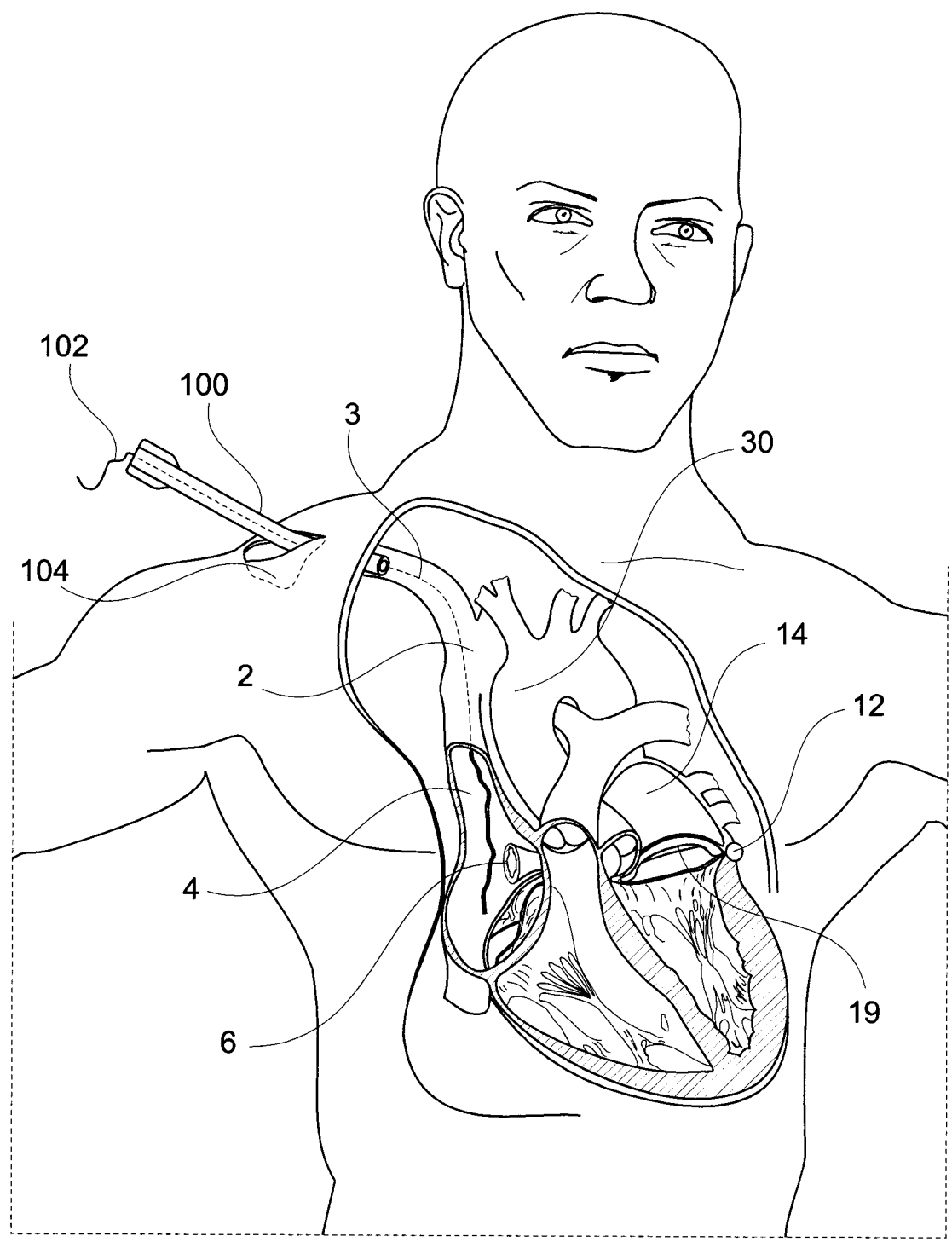
FIGS. 18, 19a-c and 20a-c are schematic illustrations that show a delivery system.

FIG. 18, and the following illustrations refer to explain a delivery system that is part of a treatment kit, the medical procedure of using the delivery system to deliver a cardiac assist device, and a medical method for therapeutically enhancing the left ventricular function of a patient permanently.

In some particular embodiments, the remote energy source is located in the fatty tissue under the skin, adjacent to a vessel, preferably a large vein. This allows for convenient access to the heart. Alternatively, the energy source may be attached to the clavicle (not shown) in order to prohibit dislocation of the same when delivering mechanical energy to the cardiac assist device inside the heart. A pocket or pouch 104 in subcutaneous tissue may be created close to the actual access vessel, e.g. the subclavian vein, see FIG. 18.

Figure 19A:
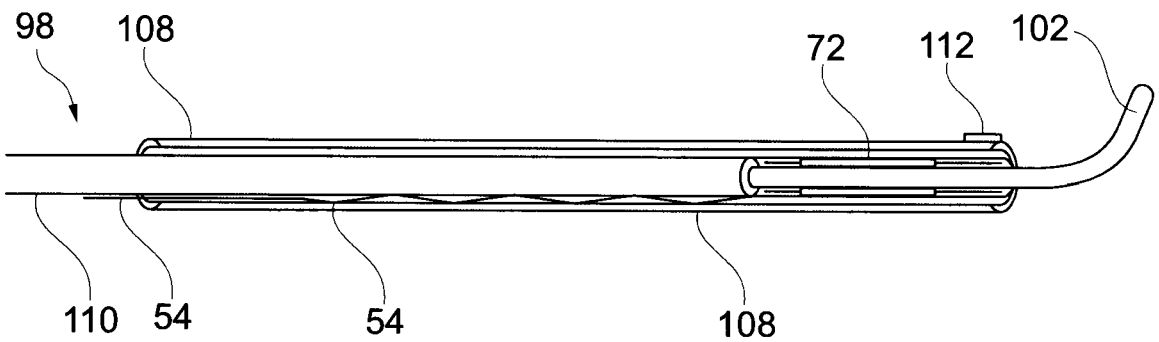
Figure 19B:
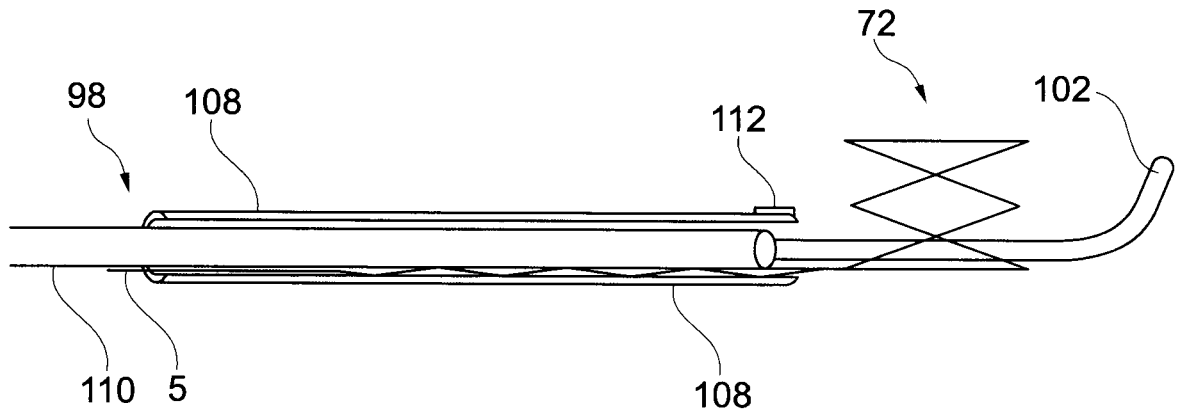
Figure 19C:
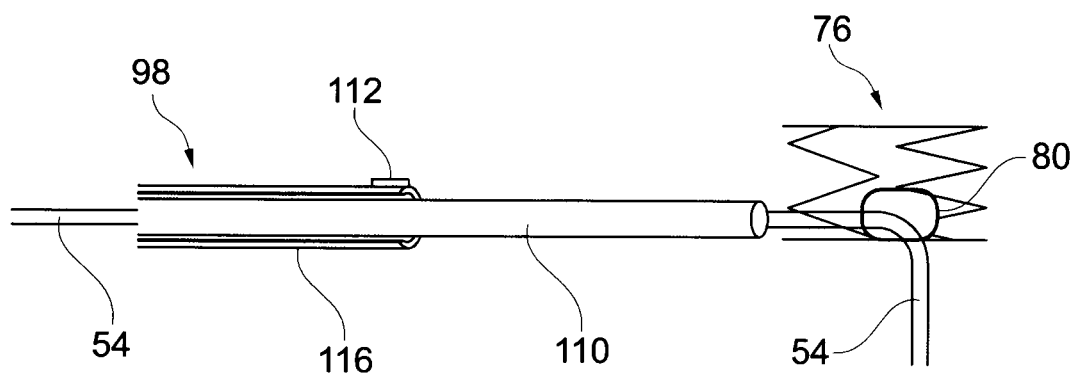
Figure 20A:
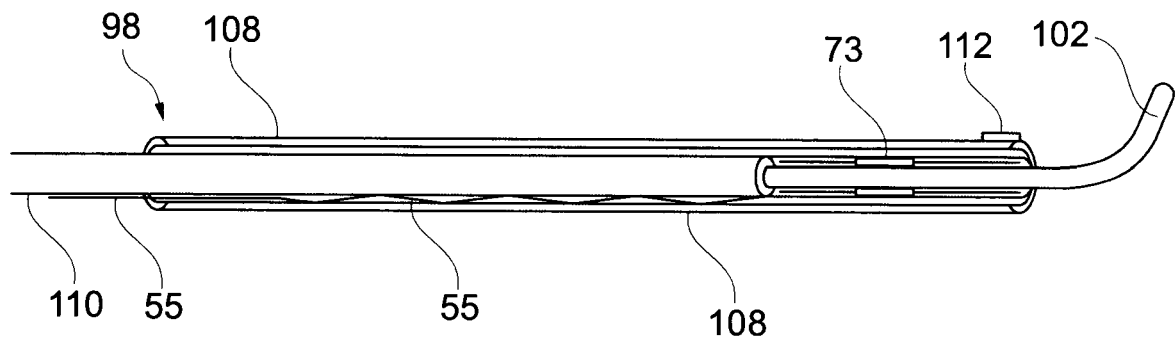
Figure 20B:
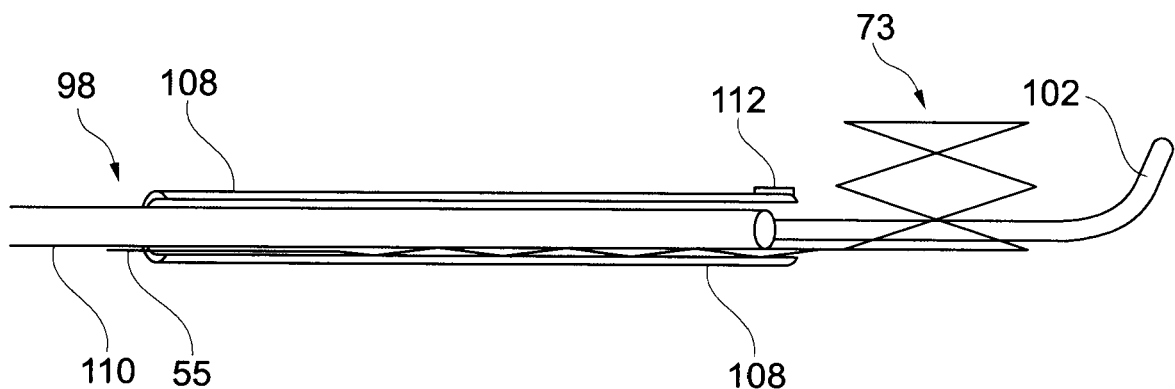
Figure 20C:
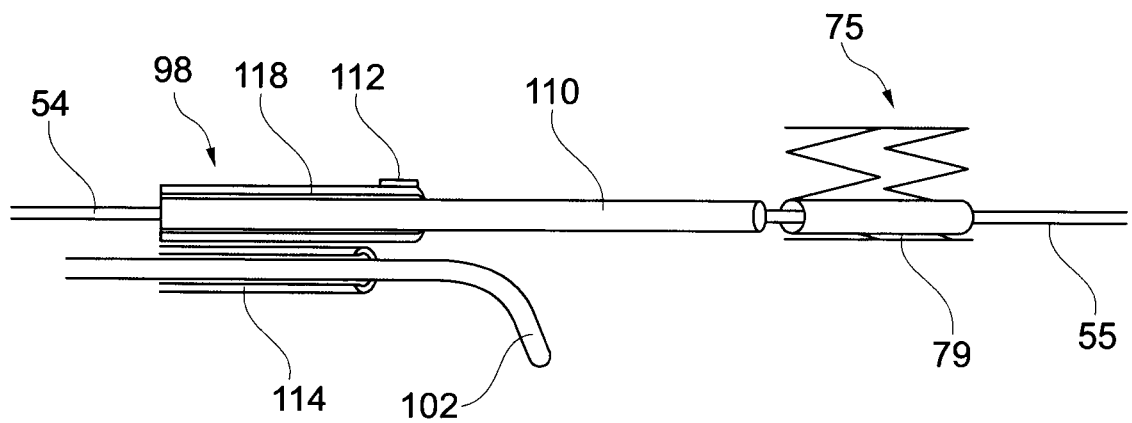

In FIG. 18 the heart is shown relative to the great vessels and the skin surface. An introducer catheter 100 with a valve (not shown) is penetrating the skin and enters a large vein, in this case the subclavian vein 3, however any other large enough vein can be used for access. Adjacent to the skin puncture site a pouch 104 may be created under the skin in the fatty tissue in order to accommodate a remote energy source 84 (not shown). The energy source may be attached to the clavicle (not shown) in order to prohibit dislocation of the same when delivering mechanical energy to the cardiac assist device inside the heart. A guide wire 102 is advanced through the introducer catheter 100 to the right atrium 4. By means of a guiding catheter 106 (first shown in FIG. 21) access to the coronary sinus is obtained via the RA and the guide wire is guided to the appropriate side branch of the coronary sinus vein system. In addition to the guide catheter, the kit contains delivery catheters where the different parts are loaded. FIGS. 19 and 20 show examples of delivery systems, however, only depicting the principle of delivering the device. FIGS. 19*a-c* show how a push and pull system is delivered from the delivery system 98.

In FIG. 19a a delivery system for a cardiac assist device as described above with reference to FIG. 10a is shown. The delivery system comprises a delivery catheter 108 that has a distal anchor 72 loaded inside at the tip. A pusher tube 110 that has a smaller outer diameter than the inner diameter of the delivery catheter may be advanced axially forward inside the delivery catheter 108 in order to push the anchor 72 out of the delivery catheter 108 at the desired site. Alternatively, the delivery catheter 108 may be retracted over the pusher catheter in order to deliver the device without any axial movement. The distal anchor unit 72, here shown as a self expanding stent, is attached to the extension unit 54 and space is accommodated inside the delivery catheter for the extension unit 54 to be able to extend until outside the patient, see FIG. 19b. The pusher tube 110, accommodates a lumen for the guide wire 102 that also is permitted to run through the anchor 72. The distal anchor unit is released and expands such that it safely anchors into the surrounding vessel tissue. Thus the distal anchor is in place, having the extension unit 54 extending therefrom.

Once the first anchor is in place, a second delivery catheter 116, shown in FIG. 19c is advanced over the extension 54 until the guiding unit 80 is aligned with the side branch in which the distal anchor 72 is located. When holding the pushing catheter 110 still in this position and retracting the deliver catheter 116, the anchor 76 may be exactly released with the guiding unit facing towards the side branch. Another aid in placing the device exactly is an X-ray marker 112 attached to the catheter in order to better visualize the exact position of the catheter, e.g. by means of fluoroscopy.

FIG. 20 depict positioning of a device where rotational force is transferred to the coronary sinus. This delivery catheter 118 is similar to the one shown in FIG. 19, except that it may have another lumen added in order to accommodate an extra guide wire 102. Any additional figures of the delivery systems accommodating other embodiments are not provided, since it would show variations that are apparent to the skilled person when reading the present disclosure.

The FIGS. 21-25 illustrate the method 800 of inserting a cardiac assist system for permanent heart function augmentation.

Figure 21A:
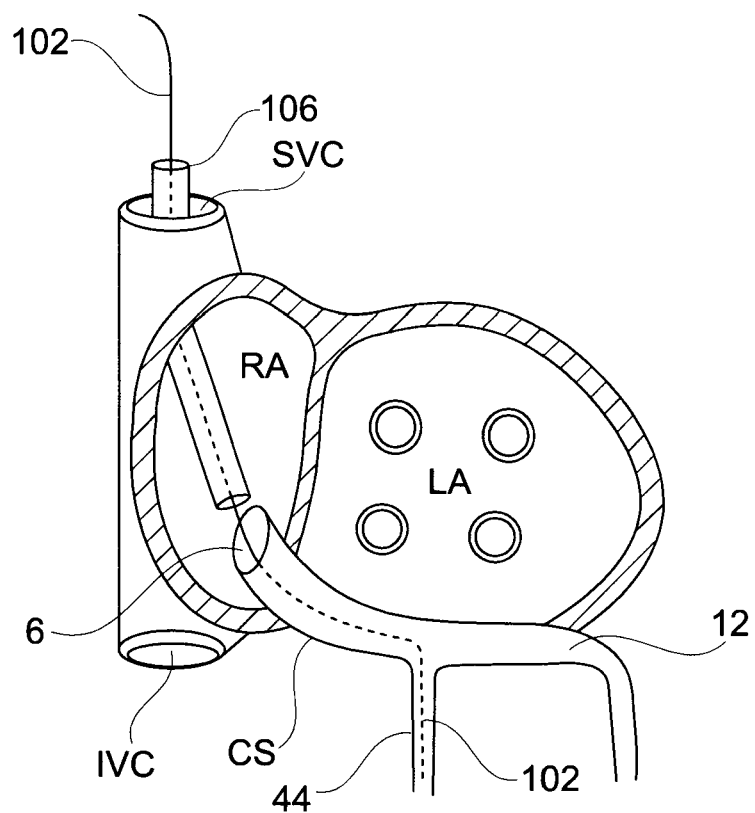
FIGS. 21a-b, 22, 23 and 24a-b are schematic illustrations that explain a method of delivering an augmentation system.

The skin is penetrated and an introducer catheter 100 with a valve (not shown) is introduced into a large vein, e.g. the subclavian vein 3, in step 800. Any other large enough vein may be used for access. A guide wire 102 is advanced through the introducer catheter 100 to the right atrium 4. By means of a guiding catheter 106 access to the coronary sinus is obtained via the RA and the guide wire is guided to the appropriate side branch of the coronary sinus venous system in step 810. FIG. 21a illustrates the advancement of a guide wire 102 into a desired side branch 44 by means of the guiding catheter 106.

Figure 21B:
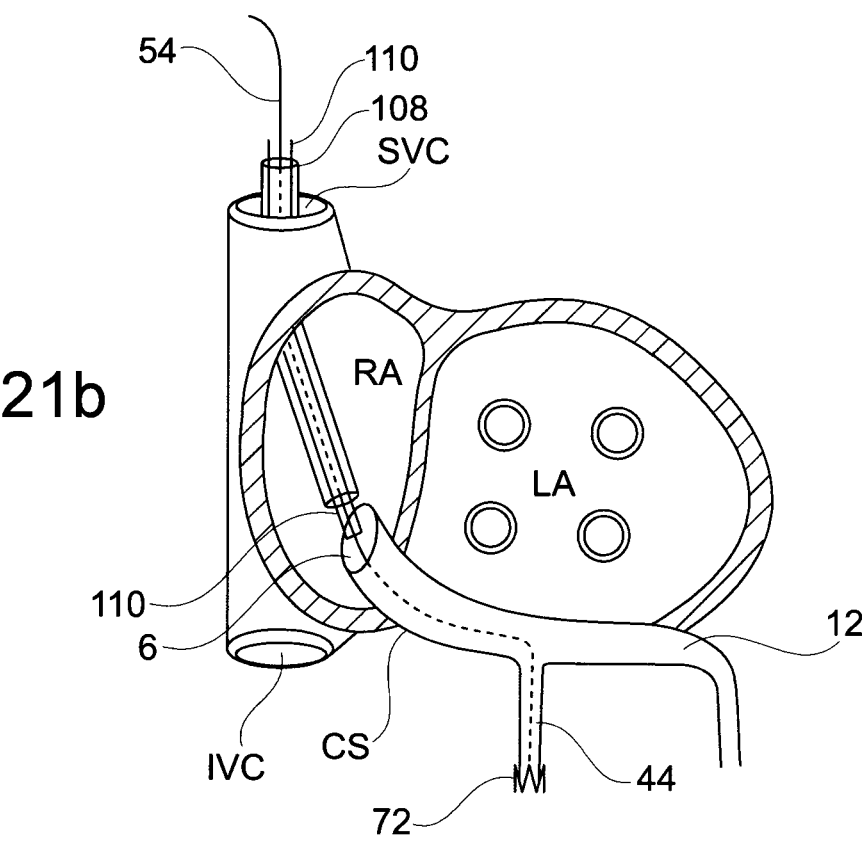

In step 820, as illustrated in FIG. 21b, the distal anchor 72 is released by means of the delivery catheter 108 in the side branch 44.

Figure 22:
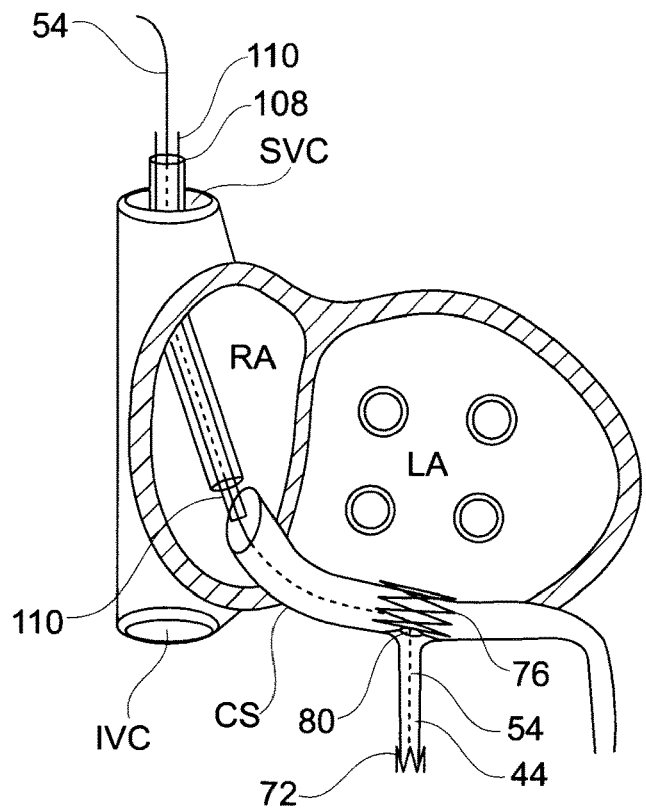

In step 830, as shown in FIG. 22, the proximal anchor 76 is positioned at the opening of the side branch.

Figure 23:
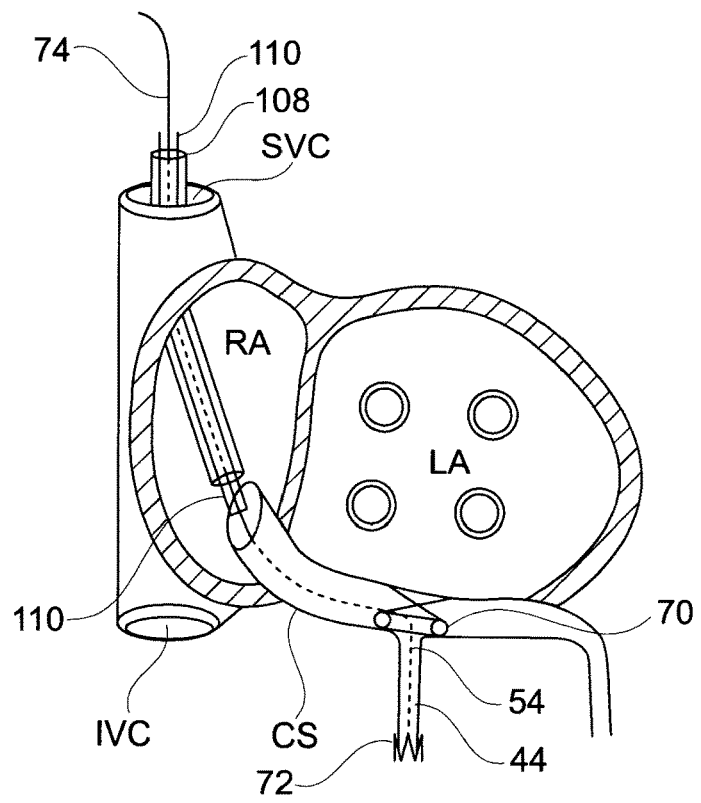

In FIG. 23 the positioning of a mini motor 70 by means of the delivery catheter 108 is shown.

Figure 24A:
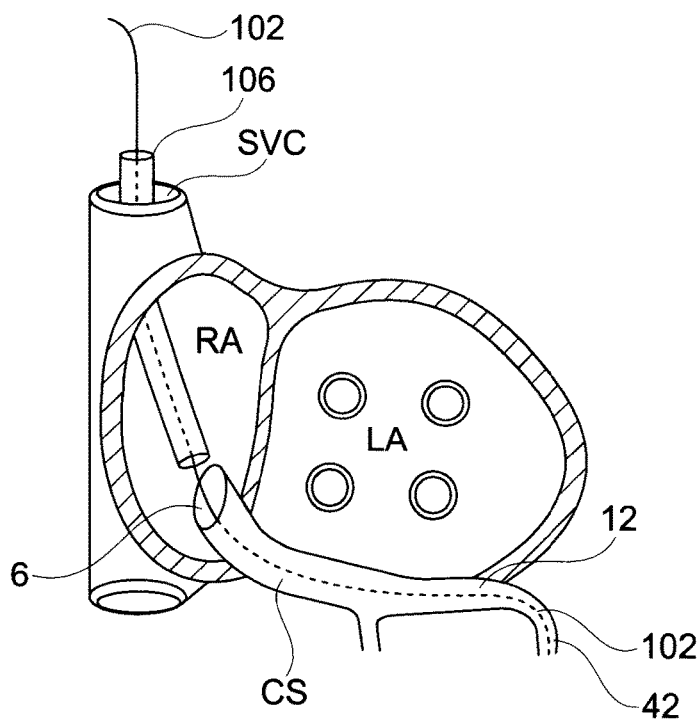
Figure 24B:
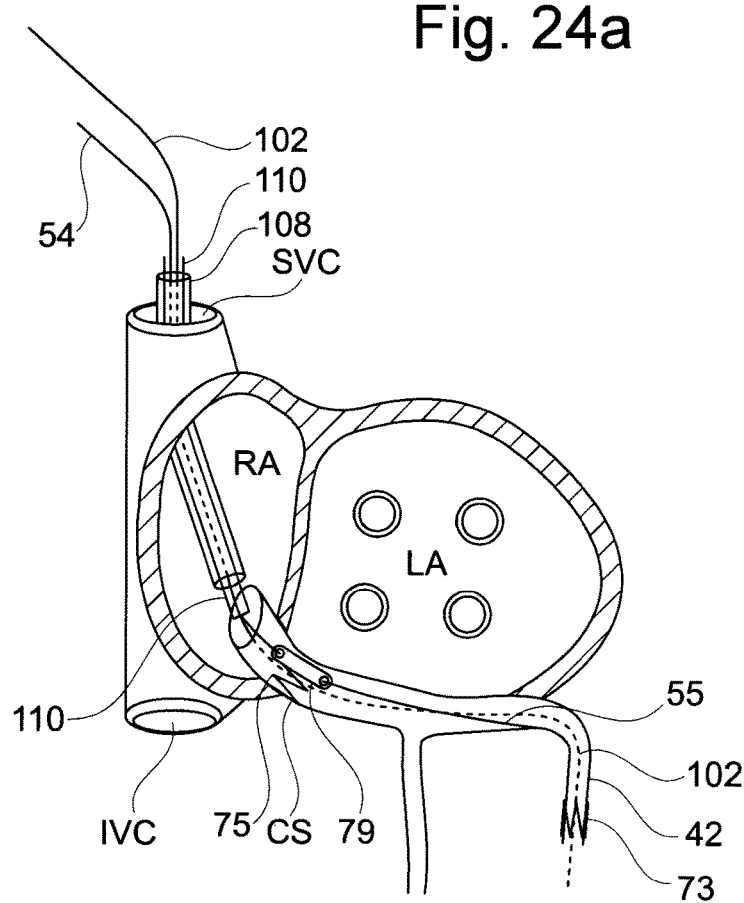
Figure 25:
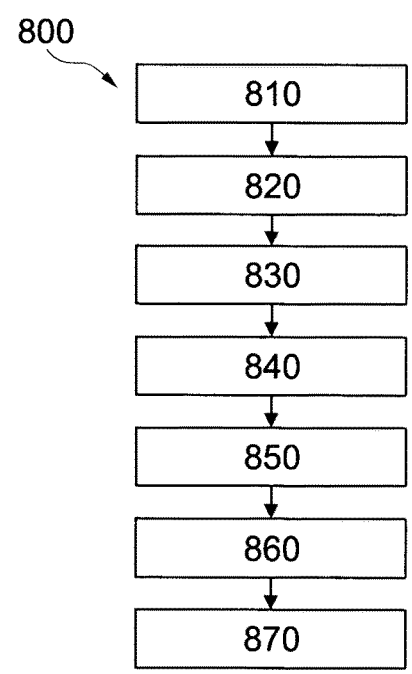
FIG. 25 is a flowchart of the method.

Finally, as shown in FIGS. 24a and b, the positioning of a rotation device is depicted. In FIG. 24a, it is shown how the guide wire is advanced into the anterior inter-ventricular vein 42 by means of the guide wire 102 and the guide catheter 106. In FIG. 24b both anchors are depicted in place, showing the loop 55. An additional guide wire may be accommodated through a separate lumen 114 (in FIG. 20c).

In step 840, adjacent to the skin puncture site a pouch 104 is created under the skin in the fatty tissue in order to accommodate a remote energy source 84 (not shown). In step 850, the energy source may be attached to the clavicle (not shown) in order to prohibit dislocation of the same when delivering mechanical energy to the cardiac assist device inside the heart.

Once both anchors are securely attached, the extension unit 54 is adjusted in length and attached to the remote energy source 84 in step 860, and the system may be activated in step 870. The remote energy source has a unit to detect the natural action of a heart, e.g. based on an electrocardiogram, a blood pressure wave, acoustic heart activity, or blood flow. The remote energy source may thus provide energy for the distance change between the two anchors in synchrony with the natural heart cycle, thereby enhancing the natural up and down movement of a mitral valve during a heart cycle.

A method is provided for permanently enhancing left ventricular pump function of a heart of a patient, the method comprising controlled assisted mitral valve plane movement synchronized with a cardiac cycle of the heart.

Concurrently filed patent application titled "A DEVICE AND A METHOD FOR AUGMENTING HEART FUNCTION" claiming priority to U.S. Provisional Application Ser. No. 61/317,631 filed Mar. 25, 2010, and Swedish application Ser. No. SE1050283-9 filed Mar. 25, 2010, both entitled Device and a Method for Augmenting Heart Function of the same applicant as the present application, which all are incorporated herein by reference in their entirety for all purposes. This co-pending application discloses devices and methods to intra-cardially move the mitral plane for augmenting the left ventricular pumping effect. Embodiments of the present disclosure may be combined with embodiments of the co-pending application. For instance an annuloplasty ring may me provided as a mitral valve intra-atrial or intra-ventricular anchor unit with a CS anchor unit or driving unit as described above. Prosthetic MV may be provided in combination with CS anchor unit or driving unit, etc. The MV plane may advantageously be well mechanically and stable be provided and moved more efficiently.

The present invention has been described above with reference to specific embodiments. However, other embodiments than the above described are equally possible within the scope of the invention. Different method steps or a different order than those described above may be provided within the scope of the invention. The different features and steps of the invention may be combined in other combinations than those described. Several actuating principles may be combined with each other in certain embodiments, e.g. a linear actuator and magnetic driving. The scope of the invention is only limited by the appended patent claims.

The invention claimed is:

1. A medical device for mimicking at least a portion of left ventricular pump action in a heart of a patient comprising:
   a first anchor unit configured for implantation in a cardiac vessel of said heart in proximity to a mitral valve (MV) plane;
   a second anchor unit configured for implantation at a location spaced apart from said first anchor unit by a distance, and in communication with said first anchor unit; and
   a powered force generating unit that generates linear anchor forces that move the first and second anchor units relative to each other, thereby shortening said distance, during successive systolic heart events.

2. The device of claim 1, wherein said powered force generating unit further generates anchor forces that move the first and second anchor units relative to each other, thereby lengthening said distance, during successive diastolic heart events.

3. The device of claim 1, wherein said powered force generating unit is operatively connected to an external energy source to receive energy therefrom and is configured to controllably provide said anchor forces.

4. The device of claim 1, wherein said first anchor unit has an expandable stent structure for anchoring said first anchor unit in said cardiac vessel.

5. The device of claim 1, wherein said first anchor unit has at least one tissue anchoring element.

6. The device of claim 1, wherein said powered force generating unit is an actuating unit for providing said anchor forces as mechanical forces, and wherein said first anchor unit and said actuating unit are in communication via a connecting unit for transferring said anchor forces and assisting a natural movement of said mitral valve plane toward and away from an apex of said heart such that left ventricular pump action is mimicked.

7. The device of claim 1, wherein said first anchor unit is positionable in one of the coronary sinus (CS), the great cardiac vein (GCV), and in a branch vessel thereof of the GCV of said heart, and wherein said second anchor unit is positionable in one of said CS, the GCV, and a branch vessel of the GCV.

8. The device of claim 1, further comprising a remote energy source, a control unit, and a sensor for measuring physiological parameters related to the cardiac cycle and for generating a sensor signal, wherein said control unit controls said force generating unit to provide movement based on said sensor signal.

9. The device of claim 8, wherein said remote energy source is comprised of a mechanical section for generating at least one of a rotational motion and a linear motion, and an extension unit extending from said mechanical section, wherein said mechanical section is said force generating unit and wherein said motion is transferred in operation of said mechanical section to said first anchor unit for movement of said mitral valve plane via said extension unit.

10. The device of claim 8, wherein said control unit is configured to set at least one of a frequency, a speed, and a pause time duration of said anchor forces.

11. A kit for improving left ventricular pump function of a heart comprising said device according to claim 1, and a delivery system suitable for inserting said device into a patient including a guide wire, a guiding catheter, and an introducing catheter.

12. A medical device for mimicking at least a portion of left ventricular pump action in a heart of a patient comprising:

a first anchor unit configured for implantation in a cardiac vessel of said heart in proximity to a mitral valve (MV) plane, a second anchor unit configured for implantation at a location different from said first anchor unit and in communication with said first anchor unit, and a powered force generating unit that generates first and second linear anchor forces that move the first and second anchor units relative to each other according to a set sequence;

wherein said set sequence comprises said first anchor forces that move said anchor units toward each other during systole and said second anchor forces that move said anchor units away from each other during diastole.

13. The device of claim 12, wherein said powered force generating unit is operatively connected to an external energy source to receive energy therefrom and to controllably provide said anchor forces.

14. The device of claim 12, wherein said first anchor unit has an expandable stent structure for anchoring said first anchor unit in said cardiac vessel.

15. The device of claim 12, wherein said first anchor unit has at least one tissue anchoring element.

16. The device of claim 12, wherein said powered force generating unit is an actuating unit for providing said anchor forces as mechanical forces, and wherein said first anchor unit and said actuating unit are in communication via a connecting unit for transferring said anchor forces and assisting a natural movement of said mitral valve plane toward and away from an apex of said heart such that left ventricular pump action is mimicked.

17. The device of claim 12, wherein said force generating unit is positionable in one of said heart, inside a side branch of the vein system on a left ventricular wall of said heart, in the left ventricle, in a right ventricle, in a right atrium, in a left atrium of said heart, and on a left ventricular outer wall of said heart.

18. The device of claim 12, further comprising a remote energy source, a control unit, and a sensor for measuring physiological parameters related to the cardiac cycle and for generating a sensor signal, wherein said control unit controls said force generating unit to provide movement based on said sensor signal.

19. The device of claim 18, wherein said remote energy source is comprised of a mechanical section for generating at least one of a rotational motion and a linear motion, and an extension unit extending from said mechanical section, wherein said mechanical section is said force generating unit and wherein said motion is transferred in operation of said mechanical section to said first anchor unit for movement of said mitral valve plane via said extension unit.

* * * * *